(12) United States Patent
Shrawat et al.

(10) Patent No.: US 8,198,460 B2
(45) Date of Patent: Jun. 12, 2012

(54) PROCESS FOR PREPARATION OF LETROZOLE AND ITS INTERMEDIATES

(75) Inventors: Vimal Kumar Shrawat, Sahibabad (IN); Jai Pal Singh, Sahibabad (IN); Rajesh Prasad Nautiyal, Sahibabad (IN)

(73) Assignee: Fresenius Kabi Oncology Ltd. (IN)

( * ) Notice: Subject to any disclaimer, the term of this patent is extended or adjusted under 35 U.S.C. 154(b) by 23 days.

(21) Appl. No.: 12/681,176

(22) PCT Filed: Jan. 16, 2008

(86) PCT No.: PCT/IN2008/000024
§ 371 (c)(1),
(2), (4) Date: Apr. 1, 2010

(87) PCT Pub. No.: WO2009/069140
PCT Pub. Date: Jun. 4, 2009

(65) Prior Publication Data
US 2010/0234617 A1    Sep. 16, 2010

(30) Foreign Application Priority Data

Nov. 28, 2007 (IN) .......................... 2479/DEL/2007

(51) Int. Cl.
*C07D 249/08* (2006.01)
*C07D 401/06* (2006.01)

(52) U.S. Cl. .................................... 548/262.2
(58) Field of Classification Search ............... 548/262.2
See application file for complete search history.

(56) References Cited

U.S. PATENT DOCUMENTS

| 4,978,672 | A | 12/1990 | Bowman et al. |
| 5,352,795 | A | 10/1994 | Bowman et al. |
| 2005/0209294 | A1 | 9/2005 | Wadhwa et al. |
| 2006/0128775 | A1 | 6/2006 | Patel et al. |
| 2007/0054964 | A1* | 3/2007 | Tatapudy et al. ............. 514/651 |
| 2007/0066831 | A1 | 3/2007 | MacDonald et al. |
| 2007/0100149 | A1 | 5/2007 | Palle et al. |
| 2007/0112202 | A1 | 5/2007 | Friedman et al. |
| 2007/0112203 | A1 | 5/2007 | Hasson et al. |
| 2009/0270633 | A1 | 10/2009 | Pathi et al. |

FOREIGN PATENT DOCUMENTS

| WO | 2005/047269 | 5/2006 |
| WO | 2007/074474 | 12/2006 |
| WO | WO/2007/0054964 | * 3/2007 |
| WO | 2007/039912 | 4/2007 |
| WO | 2007/054964 | 5/2007 |
| WO | 2007/090464 | 8/2007 |
| WO | WO 2007/090464 | * 8/2007 |
| WO | 2007/100346 | 9/2007 |

OTHER PUBLICATIONS

Patent Cooperation Treaty, "International Preliminary Report on Patentability," European Patent Office, by Officer Helps, Ian, in PCT Application No. PCT/IN2008/00024; Document of 9 pages, dated Mar. 8, 2010.
Patent Cooperation Treaty, "International Search Report," European Patent Office, by Officer Helps, Ian, in PCT Application No. PCT/IN2008/00024; Document of 3 pages, dated Aug. 5, 2008.
Shrawat et al., Response to the Written Opinion under Art 34, document of 11 pages, filed Aug. 24, 2009.

* cited by examiner

*Primary Examiner* — Susannah Chung
(74) *Attorney, Agent, or Firm* — Akerman Senterfitt; Peter A. Chiabotti

(57) ABSTRACT

The present invention relates to an improved process for preparation of the non-steroidal aromatase inhibitor drug, Letrozole of formula (I) and its intermediates, 4-[1-(1,2,4-triazolyl)methyl]-benzonitrile of formula (IV) and 4-[1-(1,2,4-triazolyl)methyl]-benzonitrile hydrochloride of formula (VII), all having a purity of ≧99%, which is simple, convenient, economical, does not use hazardous chemicals and industrially viable.

16 Claims, 2 Drawing Sheets

PROCESS FOR PREPARATION OF LETROZOLE AND ITS INTERMEDIATES

CROSS REFERENCE TO RELATED APPLICATIONS

This application is a §371 National Phase of PCT/IN2008/000024, filed Jan. 16, 2008, which claims priority to Indian Patent Application No. 2479/DEL/2007, filed Nov. 28, 2007, the entirety of both of which are herein incorporated by reference.

FIELD OF THE INVENTION

The present invention relates to an improved process for preparation of Letrozole and its intermediates, both having a purity of ≧99%, which is simple, convenient, economical and industrially viable.

BACKGROUND OF THE INVENTION

Letrozole, chemically known as 4-[alpha(4-cyanophenyl)-1-(1,2,4-triazoly)-methyl]-benzonitrile, and represented by formula (I),

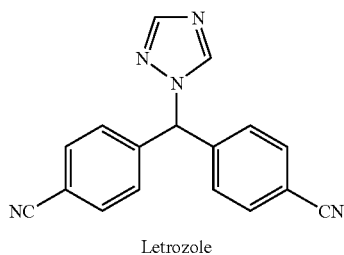

Letrozole is a therapeutically and commercially important non-steroidal aromatase inhibitor, which is widely used for adjuvant treatment of hormonally responsible breast cancer in post-menopausal women. Estrogens are produced by the conversion of androgen through the activity of aromatase enzyme, the suppression of estrogen biosynthesis in peripheral tissues and in the cancer tissue itself can therefore be achieved by specifically inhibiting the aromatase enzyme.

1. Bowman et al. were the first to disclose Letrozole in U.S. Pat. No. 4,978,672, and U.S. Pat. No. 5,352,795 and reported two methods for synthesis of Letrozole, the chemistry for Method-1 is summarized in Scheme-I.

The Method-1 for synthesis of Letrozole as disclosed by Bowman et al. in U.S. Pat. No. 4,978,672, and U.S. Pat. No. 5,352,795 and as summarized in Scheme-I, comprises reaction of alpha-bromo-4 tolunitrile or 4-bromomethyl benzonitrile (II) with 1H-1,2,4-triazole (III), in a mixture of chloroform and acetonitrile as solvent at reflux temperature for 15 hours to give 4-[1-(1,2,4-triazolyl)methyl]-benzonitrile (IV), which on reaction with 4-fluorobenzonitrile (VI) in the presence of potassium t-butoxide and in N,N-dimethylformamaide, gives crude Letrozole (I), which is recrystallized from 95% ethanol or a mixture of ether and ethyl acetate to give pure Letrozole (I).

Scheme-I: Method-1 for Synthesis of Letrozole Disclosed by Bowman et al. in U.S. Pat. No. 4,978,672 and No. 5,352,795

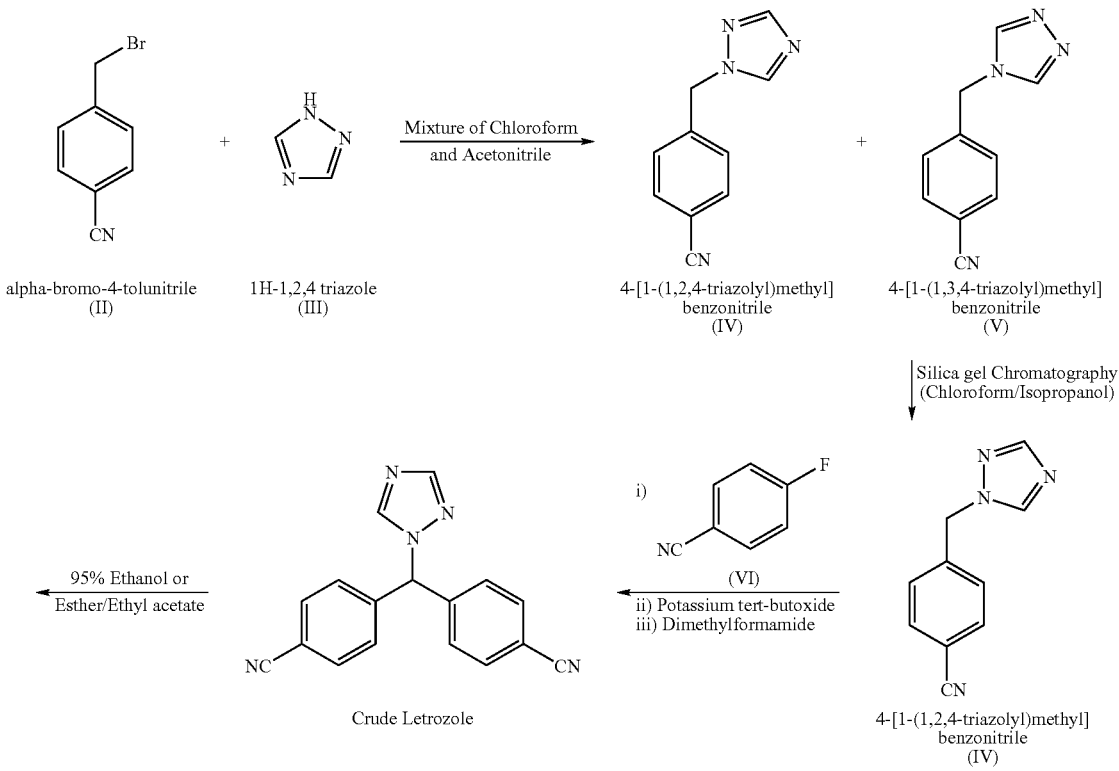

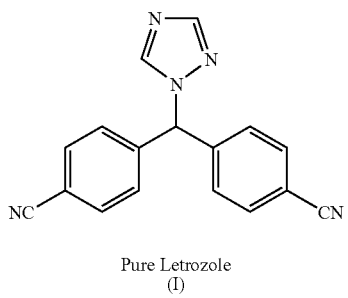

Pure Letrozole
(I)

As would be evident from Examples 9, 25, and 26 of U.S. Pat. No. 4,978,672, and U.S. Pat. No. 5,352,795, in the step reaction of alpha-bromo-4 tolunitrile or 4-bromomethyl benzonitrile (II) with 1H-1,2,4-triazole (III), as per Method-1, Scheme-I, in addition to the desired 4-[1-(1,2,4-triazolyl)methyl]-benzonitrile (IV) an appreciable amount of isomeric 4-[1-(1,3,4-triazolyl)methyl]-benzonitrile (V) is also formed in the reaction, which necessitates separation of the two isomers by column chromatography, subsequent to which the separated pure 4-[1-(1,2,4-triazolyl)methyl]-benzonitrile (IV) is reacted with 4-fluorobenzonitrile (VI) to give Letrozole. Example 25 of U.S. Pat. No. 4,978,672, and U.S. Pat. No. 5,352,795 further report that Letrozole obtained after recrystallization from 95% ethanol has a melting point of 181°-183° C., while Example 26 reports that Letrozole obtained after recrystallization from a mixture of ether and ethyl acetate has a melting point of 184°-185° C.

The major disadvantage and limitation of the Method-1 disclosed in U.S. Pat. No. 4,978,672, and U.S. Pat. No. 5,352,795 is that it leads to formation of appreciable amounts of the unwanted isomer i.e. 4-[1-(1,3,4-triazolyl) methyl]-benzonitrile (V), calling for tedious chromatographic techniques for its separation from the desired isomer i.e. 4-[1-(1,2,4-triazolyl)methyl]-benzonitrile (IV), which is expected to result in considerable loss and low yield of the desired isomer. Such a method, obviously, cannot be expected to be economically or commercially viable. Further, nowhere in the Specifications and Experimental Descriptions of U.S. Pat. No. 4,978,672, and U.S. Pat. No. 5,352,795 there is any mention about the yield and purity of Letrozole obtained by the method described therein. The second method, Method-2, reported by Bowman et al. in U.S. Pat. No. 4,978,672, and U.S. Pat. No. 5,352,795 is summarized in Scheme-II, which comprises of reaction of N-tert.butyl-4-bromo benzamide (1) with n-butyllithium and ethyl formate to give Bis-(4-N-tert.butyl carbamoylphenyl)methanol (2), which on reaction with thionyl chloride gives 4-(alpha-chloro-4' cyanobenzyl) benzonitrile (3). Reaction of 4-(alpha-chloro-4'cyanobenzyl)benzonitrile (3) with 1H-1,2,4-triazole (III) gives Letrozole (I).

Scheme-II: Method-2 for Synthesis of Letrozole Disclosed by Bowman et al. in U.S. Pat. No. 4,978,672 and No. 5,352,795

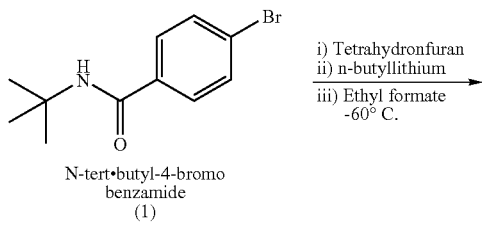

N-tert·butyl-4-bromo benzamide
(1)

i) Tetrahydrofuran
ii) n-butyllithium
iii) Ethyl formate
-60° C.

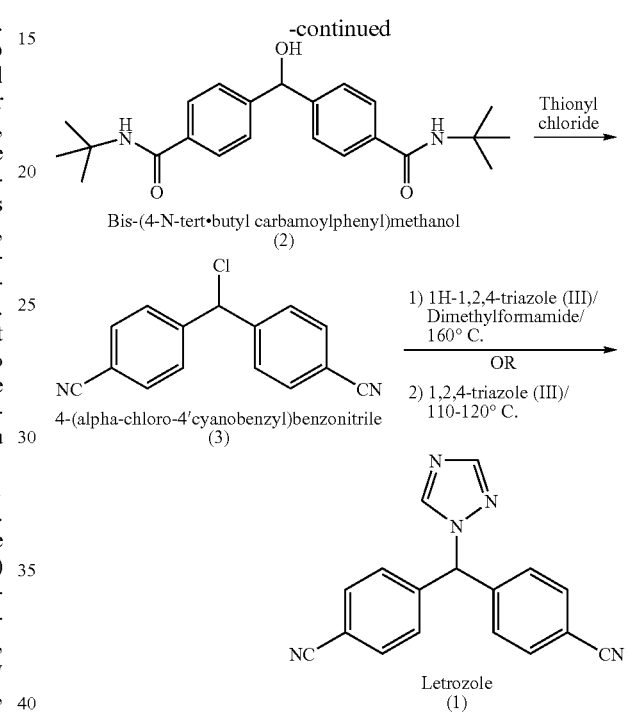

The major disadvantage and limitation of the Method-2 disclosed in U.S. Pat. No. 4,978,672, and U.S. Pat. No. 5,352,795, as evident from Examples 3, 5 and 28, described therein, is that first of all it utilizes corrosive and hazardous n-butyllithium and thionyl chloride, which require special storage, handling and disposal as well as calls for cryogenic temperatures of −60° C. and higher temperatures of about 160° C., which collectively renders the method unsafe and industrially and commercially not of particular viability. Further, as in the case of Method-1, nowhere in the Specifications and Experimental Descriptions of U.S. Pat. No. 4,978,672, and U.S. Pat. No. 5,352,795 there is any mention about the yield and purity of Letrozole obtained by the Method-2 described therein. Furthermore, the reaction of 4-(alpha-chloro-4'cyanobenzyl)benzonitrile (3) with 1,2,4-triazole (III) would most likely result in formation of the corresponding isomer along with the desired Letrozole, which would involve tedious purification techniques for its separation.

Improvements over the methods disclosed by Bowman et al. in U.S. Pat. No. 4,978,672, and U.S. Pat. No. 5,352,795 are the subject matter of the following reports, viz.

2. Wadhwa et al. in US 2005/0209294 A1, recite a method for synthesis of the intermediate 4-[1-(1,2,4-triazolyl)methyl]-benzonitrile (IV), comprising reaction of alpha-bromo-4 tolunitrile or 4-bromomethyl benzonitrile (II) with a salt of 1H-1,2,4-triazole, preferably an alkali metal salt of 1H-1,2,4-triazole (4), in a suitable solvent at a temperature of between 10° to 15° C., followed by crystallization of the isolated product. The chemistry is summarized in Scheme-III.

Wadhwa et al. in US 2005/0209294 A1, while stating that the method disclosed by Bowman et al. in U.S. Pat. No. 4,978,672, and U.S. Pat. No. 5,352,795 is not selective in that it produces the undesired isomeric 4-[1-(1,3,4-triazolyl)methyl]-benzonitrile (V) in about 50%, which as mentioned hereinbefore requires tedious chromatographic separation techniques for its removal, emphasize that by virtue of utilization of an alkali metal salt of 1H-1,2,4-triazole (4), the desired 4-[1-(1,2,4-triazolyl)methyl]-benzonitrile (IV) is obtained in >96% selectivity, thereby circumventing the utilization of tedious chromatographic techniques for its purification. Wadhwa et al., further state that the said intermediate i.e. 4-[1-(1,2,4-triazolyl)methyl]-benzonitrile (IV), obtained by their method can be converted to Letrozole of US Pharmacopoeial Quality, through conventional procedure.

While the method disclosed by Wadhwa et al. in US 2005/0209294 A1, reportedly affords the intermediate 4-[1-(1,2,4-triazolyl)methyl]-benzonitrile (IV) in >96% selectivity and further, reportedly does away with chromatographic techniques in its isolation, however, the entire Specification and the Experimental Description given in Example-1 therein, is silent about the actual yield and purity of not only the intermediate 4-[1-(1,2,4-triazolyl)methyl]-benzonitrile (IV) but also that of Letrozole obtained by the method. The industrial or commercial viability of the method, therefore, cannot be commented, in view of insufficient disclosure.

Scheme-III: Method Disclosed by Wadhwa et al. in US 2005/0209294 A1 for Synthesis of the Intermediate 4-[1-(1,2,4-triazolyl)methyl]-benzonitrile (IV) and Letrozole

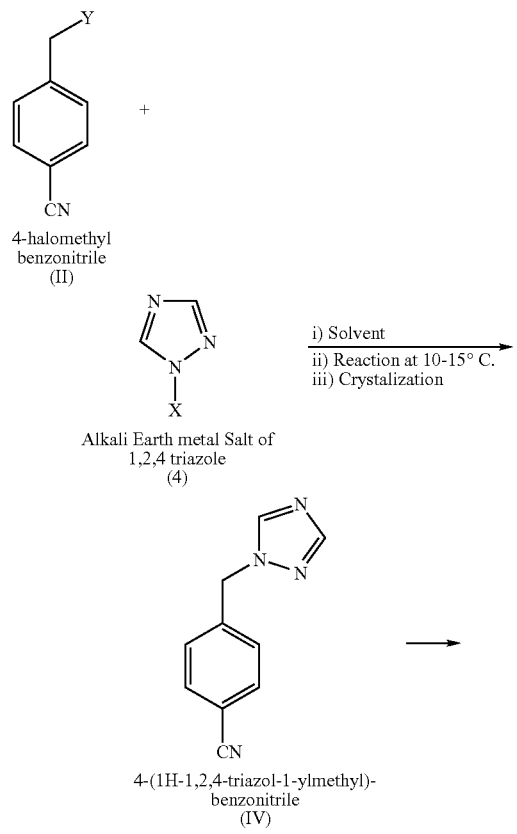

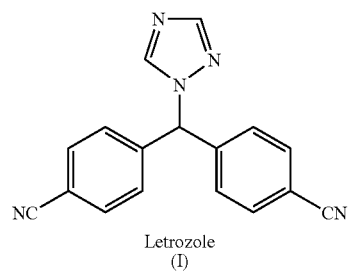

Letrozole
(I)

Y = Cl, Br, I
X = Li, Na, K
Solvent = Tetrahydrofuran, Dimethylformamide
Crystallization Solvent = Isopropyl alcohol, Toluene, Diisopropyl ether.

3. Kompella et al. in WO 2005/047269 A1, disclose a method for separation of the Letrozole precursor, 4-[1-(1,2,4-triazolyl)methyl]-benzonitrile (IV) from its isomer, 4-[1-(1,3,4-triazolyl)methyl]-benzonitrile (V), comprising treating a solution of the mixture of the two isomeric compounds (IV) and (V) in dichloromethane or chloroform with isopropylalcohol hydrochloride, followed by addition of isopropyl ether, wherein the hydrochloride salt of the undesired 4-[1-(1,3,4-triazolyl)methyl]-benzonitrile (V) precipitates out, which is removed by filtration. Basification of the filtrate, followed by evaporation of solvent and isolation of the residue from hexane or petroleum ether affords the desired 4-[1-(1,2,4-triazolyl)methyl]-benzonitrile (IV). The method is summarized in Scheme-IV.

Scheme-IV: Method Disclosed by Kompella et al. in WO 2005/047269A1 for Purification of Letrozole precursor, 4-[1-(1,3,4-triazoly)methyl] benzonitrile

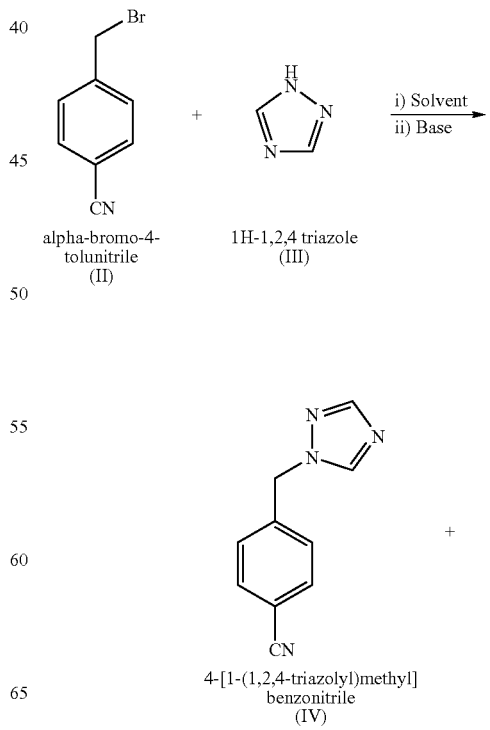

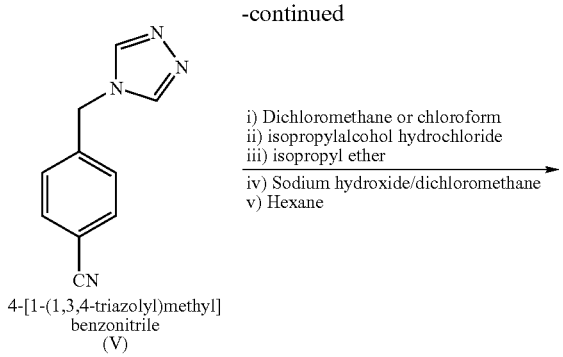

4-[1-(1,3,4-triazolyl)methyl]
benzonitrile
(V)

i) Dichloromethane or chloroform
ii) isopropylalcohol hydrochloride
iii) isopropyl ether
iv) Sodium hydroxide/dichloromethane
v) Hexane 4-[1-(1,2,4-triazolyl)methyl]
benzonitrile
(IV)

The required isomer is obtained in 47-61% yield and a purity of about 99%.

4. In another variant of the Method-1 of Bowman et al., an improved regiospecific method disclosed by Patel et al. in US 2006/0128775 A1 for synthesis of Letrozole is summarized in Scheme-V.

The method disclosed by Patel et al. in US 2006/0128775 A1 utilizes 4-amino-1,2,4-triazole (5), instead of 1H-1,2,4-triazole (III) or an alkali metal salt of 1H-1,2,4-triazole (4), as utilized by Bowman et al. in U.S. Pat. No. 4,978,672, and U.S. Pat. No. 5,352,795 and Wadhwa et al. in US 2005/0209294 A1 respectively, for reaction with alpha-bromo-4 tolunitrile or 4-bromomethyl benzonitrile (II) to give 4-[(4-amino-1,2,4-triazolium-1-yl)methyl]benzonitrile bromide (6), which on diazotisation leads to the required intermediate, 4-[1-(1,2,4-triazolyl)methyl]-benzonitrile (IV), further reaction of which with 4-fluorobenzonitrile (VI) gives crude Letrozole, which is recrystallized from polar or non-polar solvents to give pure Letrozole (I). The method of Patel et al. in US 2006/0128775 A1, in the first place provides an elegant regiospecific synthesis of Letrozole in that it like the method of Wadhwa et al. in US 2005/0209294 A1, minimizes the formation of the undesired isomeric 4-[1-(1,3,4-triazolyl)methyl]-benzonitrile (V) and also does away with tedious chromatographic separation techniques.

Scheme-V: Method Disclosed by Patel et al. in US 2006/0128775 A1 for Synthesis of Letrozole

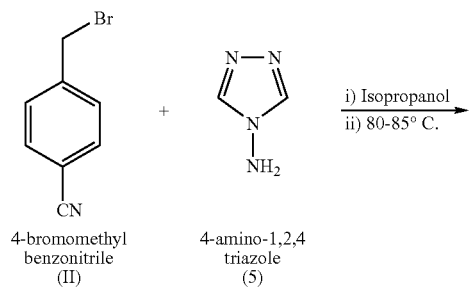

4-bromomethyl
benzonitrile
(II)

4-amino-1,2,4
triazole
(5)

i) Isopropanol
ii) 80-85° C.

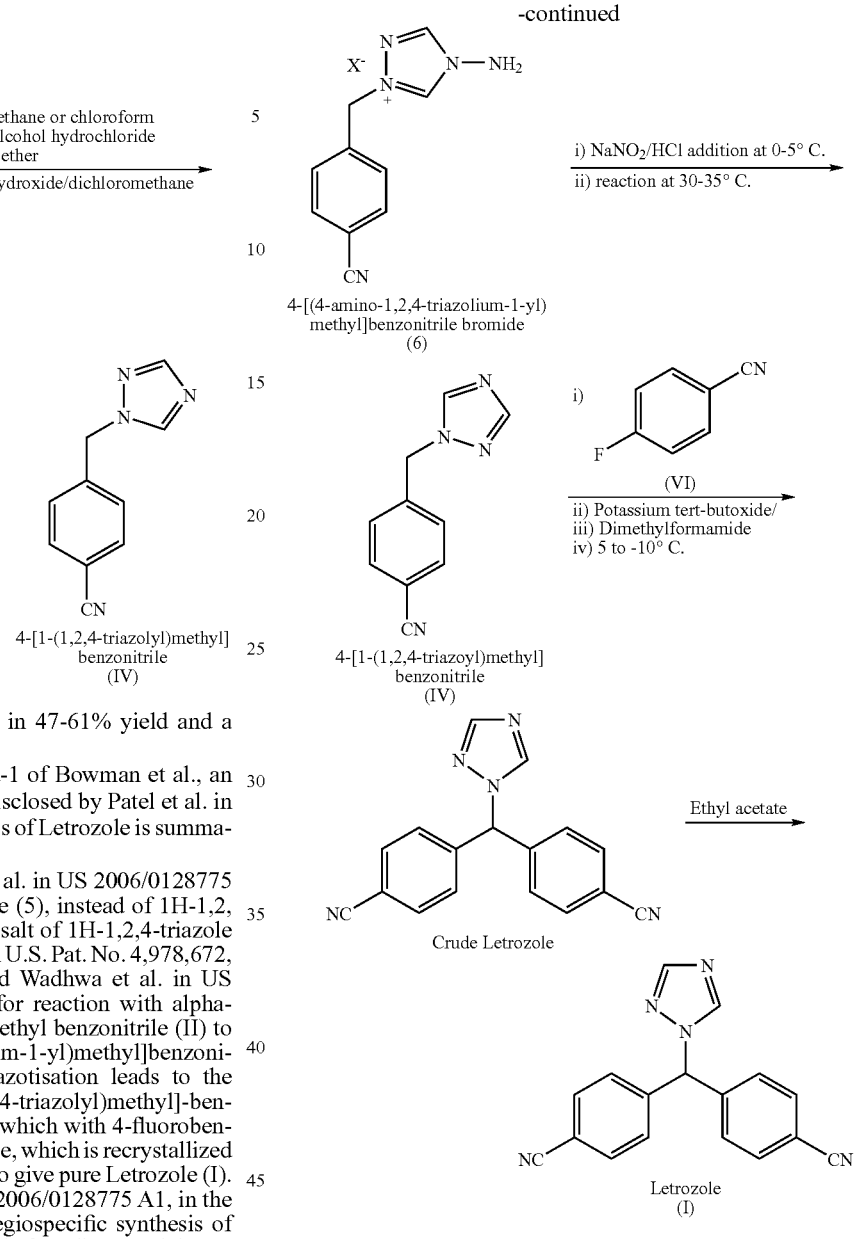

The method of Patel et al. in US 2006/0128775 A1, albeit, as evident from Example-1, described therein, reportedly gives Letrozole of 99.90% HPLC purity, however, gives Letrozole of the said purity only in an overall yield of 34%, which renders it of not being an particularly economic process. Secondly, the method comprises of an additional step of deamination of the intermediate compound (6), which in turn calls for a diazotization step, through utilization of sodium nitrite, which is hazardous and explosive, more suitable to small scale preparations rather than industrial manufacture. The method, hence, might not be particularly amenable for industrial scale-up and manufacture.

5. MacDonald et al. in US 2007/0066831 A1, report another variant of the methods disclosed by Bowman et al. in U.S. Pat. No. 4,978,672, and U.S. Pat. No. 5,352,795 and Wadhwa et al. in US 2005/0209294 A1 in that the said method, as summarized in Scheme-VI comprises:
   a) Reaction of alpha-bromo-4 tolunitrile or 4-bromomethyl benzonitrile (II) with an alkali metal salt of 1H-1,2,4- triazole (4), in presence of a solvent selected from the group consisting of diemthylacetamide, N-methyl-2-pyrrolididone, or a mixture thereof, at a temperature of about −20° to 0° C. to give 4-[1-(1,2,4-triazolyl)methyl]-benzonitrile (IV);

b) Extracting the impurities form intermediate compound (IV), in a two phase system, comprising an aqueous phase and a water-immiscible phase; and c) Reacting compound (IV) with 4-fluorobenzonitrile (VI), in presence of a solvent selected from the group consisting of dimethylformamide, diemthylacetamide, N-methyl-2-pyrrolididone, and tetrahydrofuran or a mixture thereof and a base selected from sodium bis(trimethylsilyl)amide, hexyl lithium, butyl lithium, lithium didsopropylamide, alkoxide or mixtures thereof.

US 2007/0066831 A1 further, states that the steps (a) and (b) could be combined together resulting in a one-pot synthesis of Letrozole.

In the first place, it might be mentioned herein that the chemistry disclosed by Macdonald et al. in US 2007/0066831 A1 is a nominal variation of the method disclosed by Wadhwa et al. in US 2005/0209294 A1, in that uses specific solvents such as diemthylacetamide, and N-methyl-2-pyrrolididone for formation of compound (IV) and again utilizes the same solvents for obtaining Letrozole from compound (IV), in addition to use of specific lithium containing bases, most of which are hazardous and expensive, requiring special precautions during storage, handling and disposal.

6. In yet another variation, Radhakrishnan et al. in WO 2007/039912 provide a method for synthesis of Letrozole, as summarized in Scheme-VII, which is a one-pot synthesis comprising reaction of compounds (II) and (4) to give compound (IV), which without isolation and on further reaction with compound (VI) gives Letrozole.

Scheme-VI: Method Disclosed by Macdonald et al. in US 2007/0066831 A1 for Synthesis of Letrozole

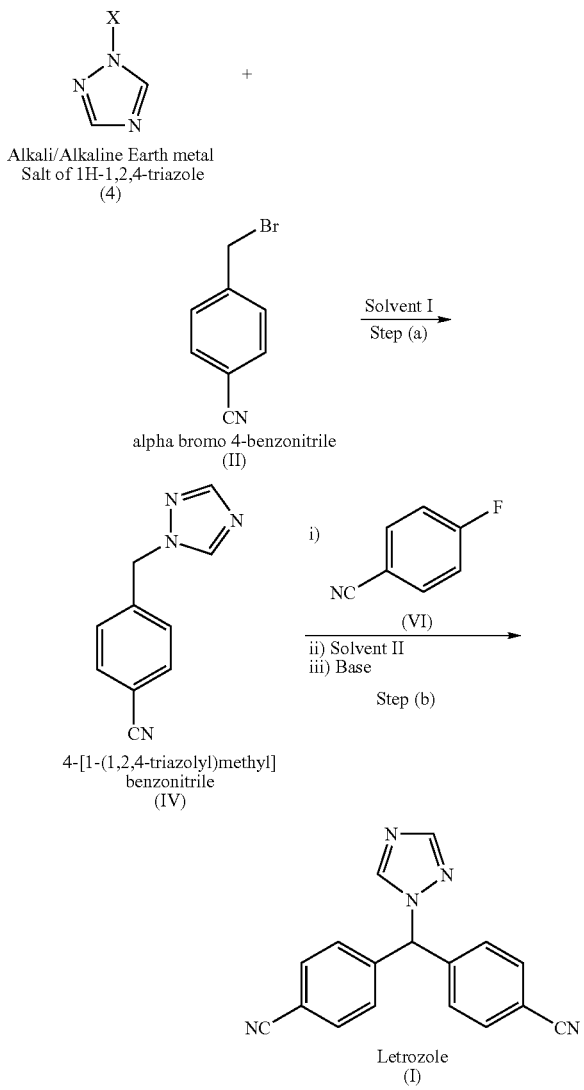

Solvent I = Dimethylformamide/Dimethylacetamide/N-Methyl-2-pyrrolidone.
Solvent II = Tetrahydrofuran/Dimethylacetamide/Dimethylformamide/N-Methyl-2-pyrrolidone
Base = Sodium bis(trimethylsilyl)amide, Hexyl lithium, Butyl lithium, Lithium diisopropylamide, Alkoxide Or Mixtures thereof.

Scheme-VII: Method Disclosed by Radhakrishnan et al. in WO 2007/039912 A1 for Synthesis of Letrozole

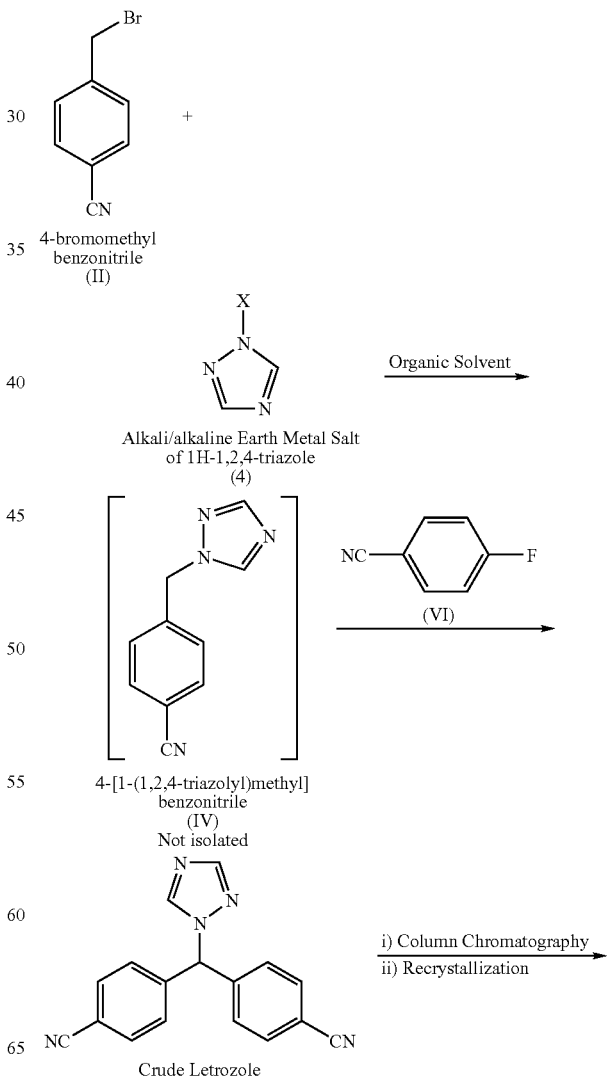

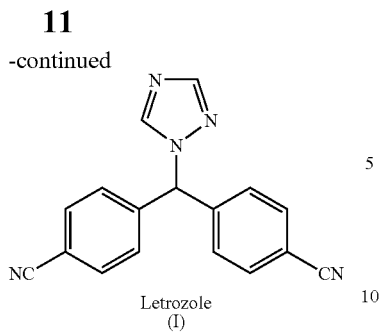
Letrozole
(I)

The major disadvantage with the method is that is still does not obliterate the use of chromatographic separation/purification of Letrozole.

7. Haider et al. in WO 2007/054964 A2 provide an improvement, as summarized in Scheme-VIII, over Method-1 disclosed by Bowman et al. in U.S. Pat. No. 4,978,672 and U.S. Pat. No. 5,352,795, in that the improvement comprises of selective removal of the isomeric 4-[1-(1,3,4-triazolyl)methyl]-benzonitrile (V), formed in the reaction of compound (II) and (III) in isopropanol as solvent, through a method of extraction, which provides the desired 4-[1-(1,2,4-triazolyl)methyl]-benzonitrile (IV), of >99% purity, and relatively free of the isomeric impurity (V).

The method of extraction, as taught by Haider et al. in WO 2007/054964 A2 comprises repeated extraction of the reaction medium containing mixture of the desired 4-[1-(1,2,4-triazolyl)methyl]-benzonitrile (IV) and the undesired 4-[1-(1,3,4-triazolyl)methyl]-benzonitrile (V) with water and a water-immiscible solvent to afford the pure 4-[1-(1,2,4-triazolyl)methyl]-benzonitrile (IV) in the organic phase, which is then further converted to Letrozole (I) of >99% purity by conventional methods. Haider et al. also teach a process for conversion of the mixture of the desired 4-[1-(1,2,4-triazolyl)methyl]-benzonitrile (IV) and the undesired 4-[1-(1,3,4-triazolyl)methyl]-benzonitrile (V) to Letrozole, from which the isomeric form of Letrozole i.e. Isoletrozole (9) so formed is removed by repeated crystallization to afford Letrozole (I) of >99% purity.

It might be noted that the method of Haider et al., primarily is one for purification of the intermediate 4-[1-(1,2,4-triazolyl)methyl]-benzonitrile (IV) as well as Letrozole (I), for removal of the corresponding isomeric impurities and as such does not provide any inputs for controlling or minimization of the formation of the isomeric 4-[1-(1,3,4-triazolyl)methyl]-benzonitrile (V) in the reaction. Secondly, the method of extraction as well as purification taught by Haider et al. is tedious, comprising multiple extractions, with multiple solvents and this coupled with the fact that it does not provide any improvement in controlling or minimization of the formation of the isomeric 4-[1-(1,3,4-triazolyl)methyl]-benzonitrile (V) in the reaction, leads to significant losses, thereby resulting in rather low yields of Letrozole (I). The method, therefore, is not of commercial significance.

Scheme-VIII: The Method Disclosed by Haider et al. in WO 2007/054964 A2 for Synthesis of Letrozole

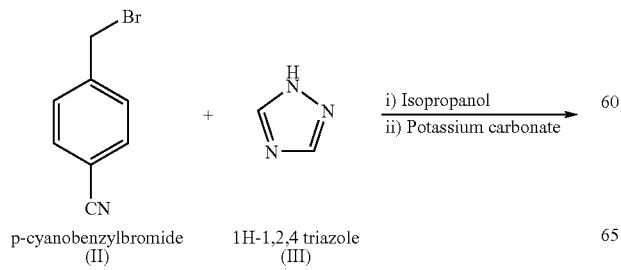

p-cyanobenzylbromide (II)    1H-1,2,4 triazole (III)

i) Isopropanol
ii) Potassium carbonate

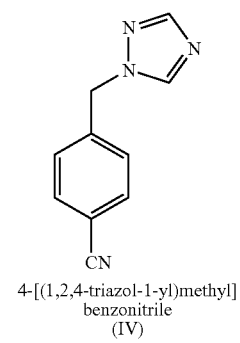

4-[(1,2,4-triazol-1-yl)methyl] benzonitrile
(IV)

+

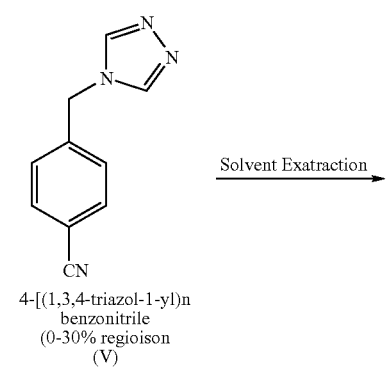

4-[(1,3,4-triazol-1-yl)n benzonitrile
(0-30% regioison
(V)

Solvent Exatraction →

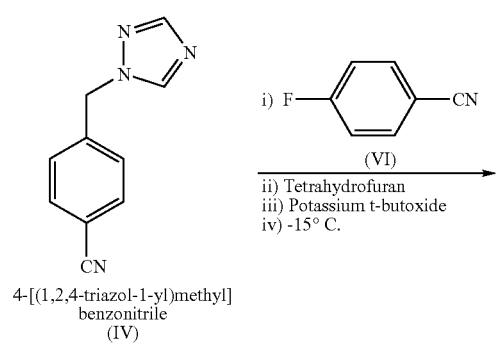

4-[(1,2,4-triazol-1-yl)methyl] benzonitrile
(IV)

i) F—⌬—CN
(VI)
ii) Tetrahydrofuran
iii) Potassium t-butoxide
iv) -15° C.

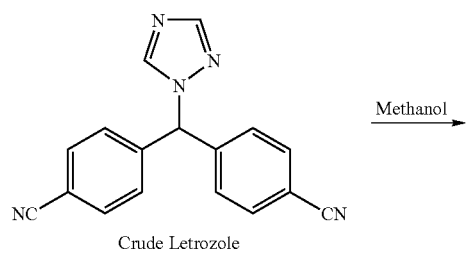

Crude Letrozole

Methanol →

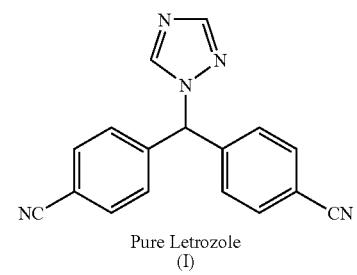

Pure Letrozole
(I)

8. Pizzocaro et al. in WO 2007/090464 A1, a process for preparation of Letrozole (I), as summarized in Scheme-IX, characterized in that it teaches either simultaneous addition of a solution of 4-[1-(1,2,4-triazolyl)methyl]-benzonitrile (IV) and a solution of 4-fluorobenzonitrile (VI) in an aprotic dipolar solvent to a solution of an alkali metal alkoxide in the same aprotic dipolar solvent or addition of an unique solution in an aprotic dipolar solvent comprising of compounds (IV) and (VI) to aprotic dipolar solvent, and reacting at a temperature of between −20° to +40° C.

The method of Pizzocaro et al., in addition to involving adherence to several critical parameters like temperature, flow rate, etc. moreover, does not provide any details of the yields and purity of Letrozole, obtained by the methods described therein.

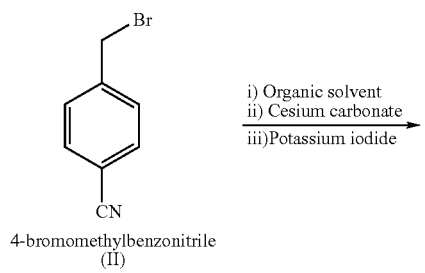

4-bromomethylbenzonitrile
(II)

i) Organic solvent
ii) Cesium carbonate
iii) Potassium iodide

Scheme-IX: Method Disclosed by Pizzocaro et al. in WO 2007/090464 A1 for Synthesis of Letrozole

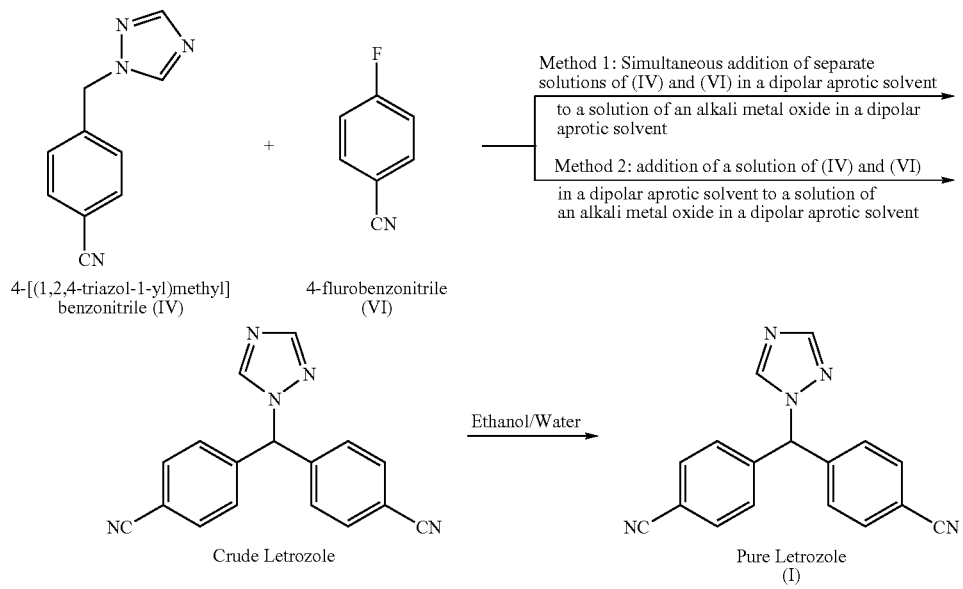

9. Srinivas et al. WO 2007/107733 A1 recite a further variation of Method-1 disclosed by et al. in U.S. Pat. No. 4,978,672 and U.S. Pat. No. 5,352,795, for synthesis of Letrozole, substantially free from its isomeric impurity, which is summarized in Scheme-X. The method comprises reacting 4-bromomethylbenzonitrile (II), with 1H 1,2,4-triazole (III) in an organic solvent in presence of cesium carbonate and precipitation of 4-[1-(1,2,4-triazolyl)methyl]-benzonitrile (IV), thus formed from the reaction medium using a suitable organic solvent. The intermediate (IV) is further converted to Letrozole by reaction with 4-fluorobenzonitrile (VI) in presence of an organic solvent and silicon amine, which are lithium, sodium, or potassium disilazanes or monosilazane.

The method utilizes sensitive and expensive silicon compounds like lithium hexamethyldisilazane, which requires highly controlled reaction conditions.

Scheme-X: Method Disclosed by Srinivas et al. in WO 2007/107733 A1 for Synthesis of Letrozole

1H-1,2,4 triazole
(III)

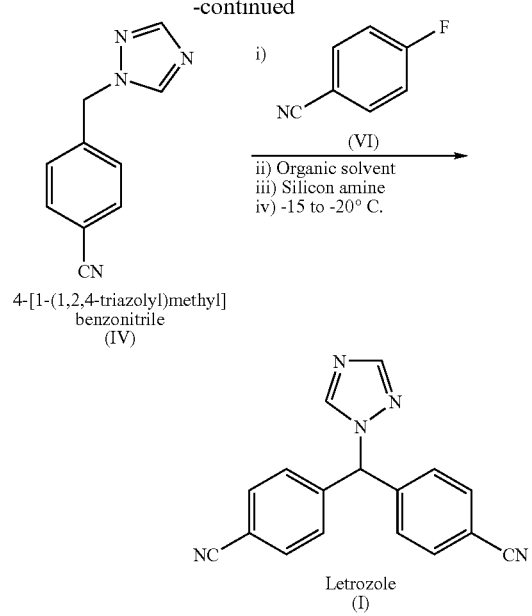

10. Hasson et al. in US 2007/0112203 A1, provide a method, as summarized in Scheme-XI, for purification of a mixture containing Letrozole (I) and its isomeric impurity i.e. Isoletrozole (IX), which is an extension of Method-2 disclosed by Bowman et al. in U.S. Pat. No. 4,978,672 and U.S. Pat. No. 5,352,795. The method takes advantage of the rapid oxidation of Isoletrozole (9) to 4,4'-dicyclobenzophenone (10), in comparison to Letrozole (I), the oxidized compound (10), being easily separable from Letrozole, can be removed by crystallization, affording pure Letrozole. The Letrozole product, in turn is prepared by Method-2 disclosed by Bowman et al. in U.S. Pat. No. 4,978,672 and U.S. Pat. No. 5,352,795. From the Enabling Disclosures of Hasson et al. in US 2007/0112203 A1, it could be seen that the method of oxidative purification of Letrozole, does not provide the said Letrozole, free of the Isoletrozole impurity (IX), directly and in fact, about 1 to 4% of Isoletrozole (IX) remains in the product, which is further removed by successive crystallizations to provide Letrozole (I) of 99.9% purity.

Scheme-XI: Method Disclosed by Hasson et al. in US 2007/011203 A1 for Synthesis of Letrozole

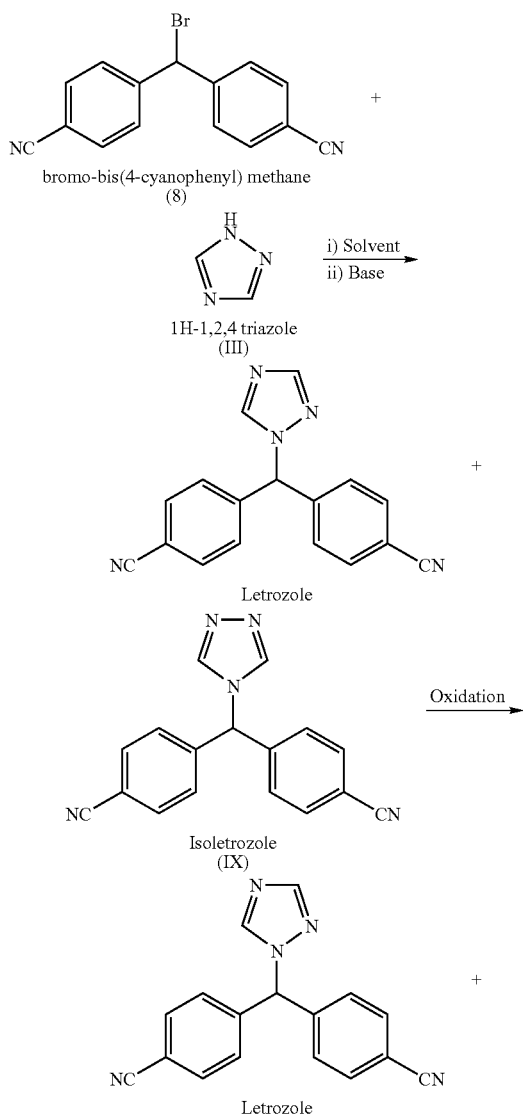

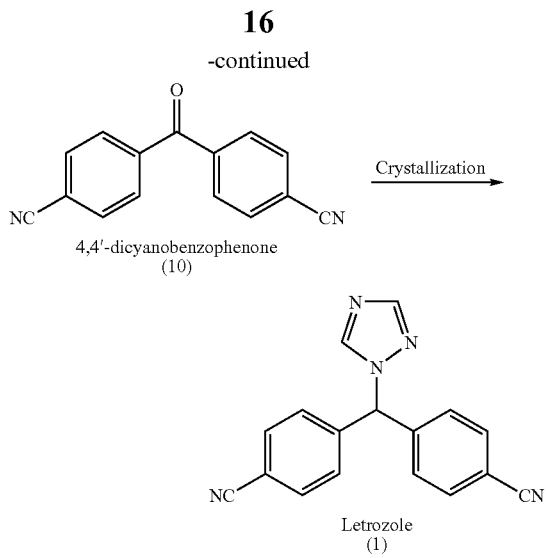

It is also noted that Letrozole to some extent also undergoes oxidation, albeit slowly, resulting in formation of additional impurities. Removal of such impurities, coupled with the task of removal of Isoletrozole (IX) and 4,4'-dicyclobenzophenone (10) results in significant yield loss, rendering the method not particularly attractive, economically.

11. Palle et al. in US 2007/0100149 A1, recite an alternate method for synthesis of Letrozole, as summarized in Scheme-XII.

Scheme-XII: Method Disclosed by Palle et al. in US 2007/0100149 A1 for Synthesis of Letrozole

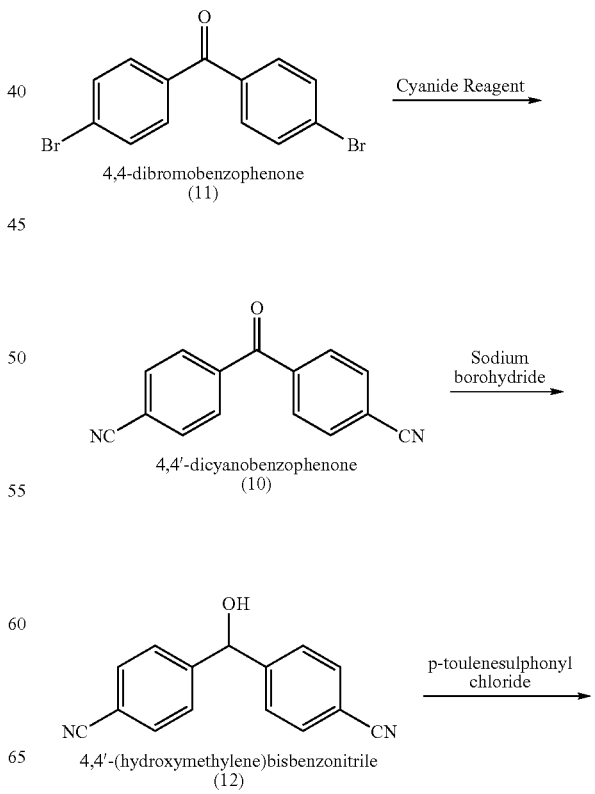

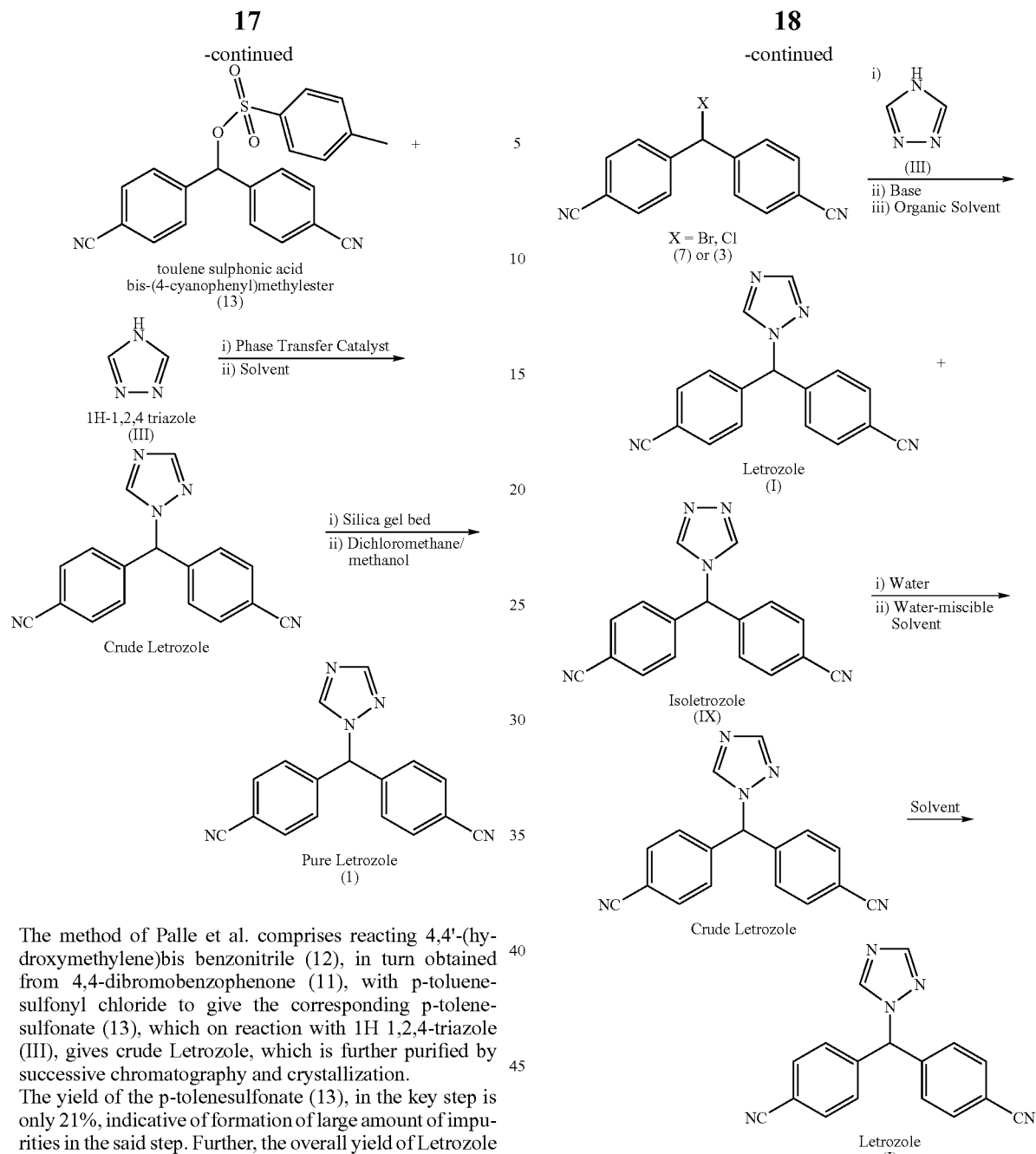

The method of Palle et al. comprises reacting 4,4'-(hydroxymethylene)bis benzonitrile (12), in turn obtained from 4,4-dibromobenzophenone (11), with p-toluenesulfonyl chloride to give the corresponding p-tolenesulfonate (13), which on reaction with 1H 1,2,4-triazole (III), gives crude Letrozole, which is further purified by successive chromatography and crystallization.

The yield of the p-tolenesulfonate (13), in the key step is only 21%, indicative of formation of large amount of impurities in the said step. Further, the overall yield of Letrozole obtained by the method is only about 14%, which would render the method not viable commercially.

12. Friedman et al. in US 2007/0112202 A1, provide an extension of Method-2 disclosed by Bowman et al. in U.S. Pat. No. 4,978,672 and U.S. Pat. No. 5,352,795, which is summarized in Scheme-XIII.

Scheme-XIII: Method Disclosed by Friedman et al. in US 2007/1112202 A1 for Synthesis of Letrozole

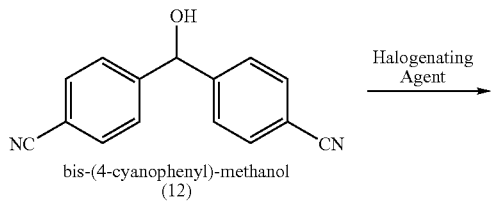

US 2007/0112202 A1 reports synthesis of Letrozole by the abovementioned method in 54-56% yield and having a HPLC purity 99.4%, which may not suit Pharmacopoeial standards, which suggests that the product obtained requires further purification, which, incidentally, is acknowledged by Friedman et al., who state that single purification using various solvents does not give Letrozole of acceptable purity, and hence multiple purifications are required to achieve the same. Needless to mention, this would result in significant loss of the precious product. Further, the novelty and inventiveness of the method is in question, since Bowman et al. in U.S. Pat. No. 4,978,672 and U.S. Pat. No. 5,352,795 have disclosed the same chemistry earlier.

13. Agarwal et al. in WO 2007/074474 A1 recite a synthesis of Letrozole, utilizing novel intermediates, the chemistry of which is summarized in Scheme-XIV.

Scheme-XIV: Method Disclosed by Agarwal et al. in WO 2007/074474 A1 for Synthesis of Letrozole

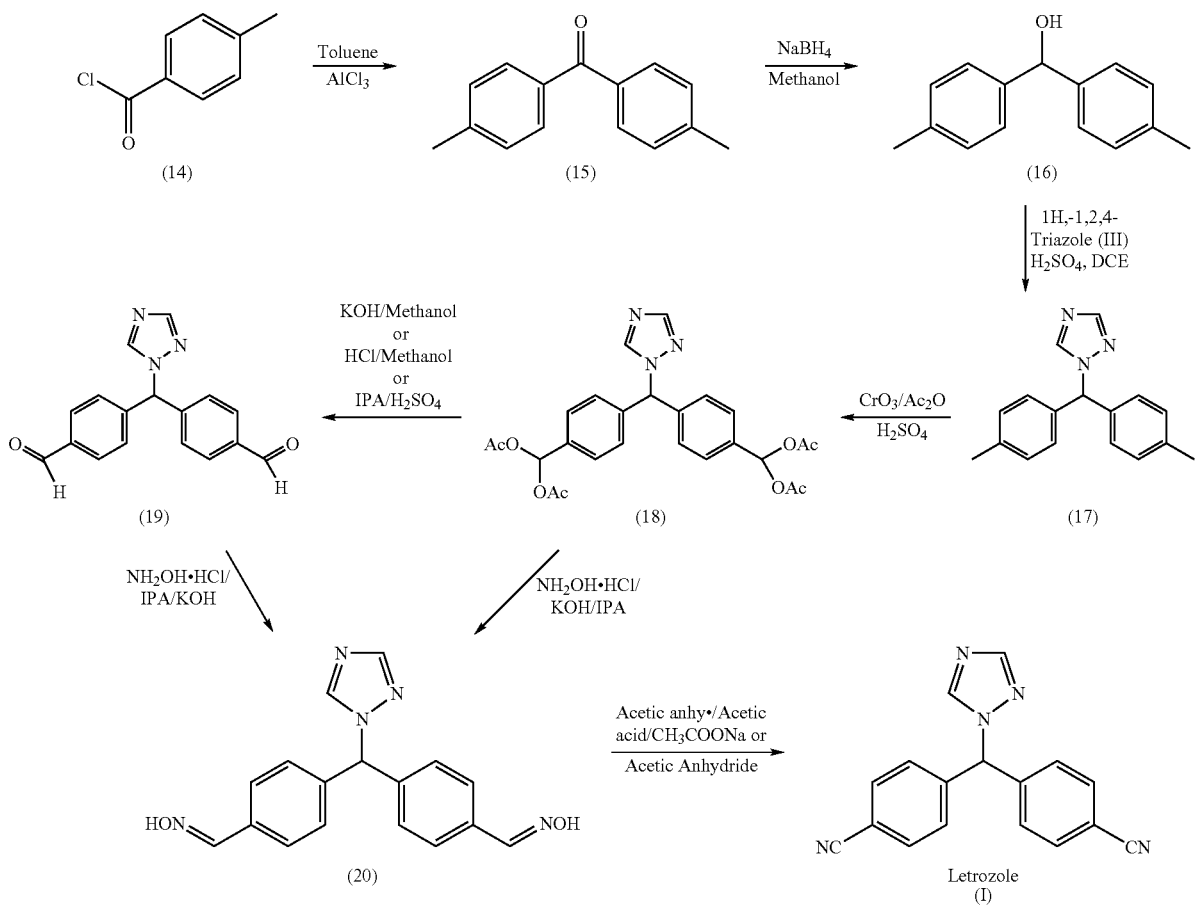

The method is lengthy and the reported overall yield of Letrozole appears to be only 9-11%.

From the foregoing, it would be abundantly evident that the prior art methods for synthesis of Letrozole and its intermediates suffer from one or more of the following limitations, viz.
i) Formation of significant amounts of the undesired isomeric 4-[1-(1,3,4-triazolyl)methyl]-benzonitrile (V) and Iso-letrozole (IX) in the reported methods;
ii) Utilization of tedious chromatographic, extraction, and/or multiple crystallization techniques for separation and removal of the said undesired isomeric impurities;
iii) Utilization of low cryogenic and high reaction temperatures for the key conversion steps;
iv) Involvement of hazardous chemical reactions like diazotization and utilization of hazardous, corrosive, and expensive chemicals and reagents like sodium nitrite, thionyl chloride, n-butyllithium, lithium amides, alkali metal silanes etc.;
v) Lengthy and multiple reaction steps;
vi) Strict adherence to critical reaction conditions and parameters;
vii) Generally moderate to low yields of Letrozole; and
viii) A product, in many instances not conforming to Pharmacopoeial requirements,
which collectively render such methods as particularly not having any significant economic, industrial or commercial viability, feasibility, advantage, application or attraction.

Considering the therapeutic and commercial importance of Letrozole, a need, therefore, exists for a method for synthesis of Letrozole, which is simple, convenient, economical, non-hazardous, industrially benign, and, moreover, overcomes the limitations associated with the prior art methods, enumerated hereinbefore.

The present invention is a step forward in this direction and provides a method for synthesis of Letrozole and its intermediates in a purity of ≧99%, which is simple, convenient, economical, and industrially viable, and moreover, overcomes most, if not all the limitations associated with the prior art methods for its synthesis.

OBJECTS OF THE INVENTION

An immediate object of the present invention is to provide a simple, convenient, economical and industrially viable process for preparation of 4-[1-(1,2,4-triazolyl)methyl]-benzonitrile (IV), in high yield and purity.

Another immediate object of the present invention is to provide a simple, convenient, economical and industrially viable process for preparation of Letrozole of formula (I), in high yield and purity, conforming to Pharmacopoeial specifications.

An object of the present invention is to provide a simple, convenient, economical and industrially viable process for preparation of 4-[1-(1,2,4-triazolyl)methyl]-benzonitrile (IV), in high yield and purity, which, moreover, is free of the limitations associated with the prior art methods for its preparation.

Another object of the present invention is to provide a simple, convenient, economical and industrially viable process for preparation of Letrozole of formula (I), in high yield and purity, which, moreover, is free of the limitations associated with the prior art methods for its preparation.

A particular object of the present invention is to provide a process for preparation of 4-[1-(1,2,4-triazolyl)methyl]-benzonitrile (IV), in high yield and purity, wherein formation of the undesired isomeric 4-[1-(1,3,4-triazolyl)methyl]-benzonitrile of formula (V) is minimized.

Another particular object of the present invention is to provide a process for preparation of Letrozole of formula (I), in high yield and purity, which is essentially free of the isomeric Isoletrozole of formula (IX).

Another object of the present invention is to provide a process for preparation of 4-[1-(1,2,4-triazolyl)methyl]-benzonitrile (IV) and Letrozole of formula (I), in high yield and purity, which does not take recourse to tedious chromatographic, multiple extractions, and multiple crystallization techniques for their preparation.

Yet another object of the present invention is to provide a process for preparation of 4-[1-(1,2,4-triazolyl)methyl]-benzonitrile (IV) and Letrozole of formula (I), in high yield and purity, which does not take recourse to utilization of hazardous chemical reactions for their preparation.

A further object of the present invention is to provide a process for preparation of 4-[1-(1,2,4-triazolyl)methyl]-benzonitrile (IV) and Letrozole of formula (I), in high yield and purity, which does not take recourse to utilization of hazardous and corrosive chemicals and reagents for their preparation.

Yet further object of the present invention is to provide a process for preparation of 4-[1-(1,2,4-triazolyl)methyl]-benzonitrile (IV) and Letrozole of formula (I), in high yield and purity, which does not take recourse to utilization of expensive chemical and reagents for their preparation.

A still further object of the present invention is to provide a process for preparation of 4-[1-(1,2,4-triazolyl)methyl]-benzonitrile (IV) and Letrozole of formula (I), in high yield and purity, which does not require strict adherence to critical reaction conditions and parameters for their preparation.

Another object of the present invention is to provide a process for preparation of 4-[1-(1,2,4-triazolyl)methyl]-benzonitrile (IV) and Letrozole of formula (I), in high yield and purity, which does not take recourse to utilization of multiple synthetic steps for their preparation.

Yet another object of the present invention is to provide a process for preparation of 4-[1-(1,2,4-triazolyl)methyl]-benzonitrile (IV), of ≧99% purity, which is simple, convenient, economical, and industrially viable.

Still another and object of the present invention is to provide a process for preparation of Letrozole of formula (I), of ≧99% purity, which is simple, convenient, economical, and industrially viable.

A further object of the present invention is to provide a process for preparation of Letrozole of formula (I), of purity of ≧99%, which is easily amenable to up gradation to Pharmacopoeial quality, through a single step of crystallization.

In their endeavours to meet the objectives, in the first place, the present inventors found that the original Method-1, as summarized in Scheme-I disclosed by Bowman et al. in U.S. Pat. No. 4,978,672 and U.S. Pat. No. 5,352,795 for preparation of the intermediate, 4-[1-(1,2,4-triazolyl)methyl]-benzonitrile (IV) could surprisingly be made to result in significant reduction in formation of the isomeric 4-[1-(1,3,4-triazolyl)methyl]-benzonitrile of formula (V), through a very simple election of a parameter, which neither contributes to an extra additional step in the process nor adds anything extra to the cost of manufacture of 4-[1-(1,2,4-triazolyl)methyl]-benzonitrile (IV), as well as Letrozole of formula (I), prepared utilizing the said intermediate (IV).

It was surprisingly found by the present inventors that in the reaction of alpha-bromo-4 tolunitrile or 4-bromomethyl benzonitrile (II) with 1H-1,2,4-triazole (III) for preparation of the Letrozole precursor, 4-[1-(1,2,4-triazolyl)methyl]-benzonitrile (IV), a very significant reduction, of more than 80%, in the formation of the undesired isomeric 4-[1-(1,3,4-triazolyl)methyl]-benzonitrile of formula (V) could be achieved simply by addition of 1H-1,2,4-triazole (III), over a period of 1 to 4 hours to a mixture of 4-bromomethyl benzonitrile (II) and an alkali metal carbonate in a suitable organic solvent, at a temperature ranging from about 20° to 50° C. The amount of the undesired isomeric 4-[1-(1,3,4-triazolyl)methyl]-benzonitrile of formula (V) formed in the reaction, through addition of 1H-1,2,4-triazole (III), over a period of 1 to 4 hours to a mixture of 4-bromomethyl benzonitrile (II) and an alkali metal carbonate in a suitable organic solvent was found to be only about 6-8%, in comparison to formation of the same in about 30-45%, when either 1H-1,2,4-triazole (III), is added in one lot or over a period less than 1 hour to a solution of 4-bromomethyl benzonitrile (II) in a suitable organic solvent.

Further, it was found that the level of 6-8% of the isomeric 4-[1-(1,3,4-triazolyl)methyl]-benzonitrile of formula (V), formed in the reaction could be practically removed on isolation of the product i.e. 4-[1-(1,2,4-triazolyl)methyl]-benzonitrile (IV), as its hydrochloride salt i.e. 4-[1-(1,2,4-triazolyl)methyl]-benzonitrile hydrochloride of formula (VII). Typically, it was found that the isolated 4-[1-(1,2,4-triazolyl)methyl]-benzonitrile hydrochloride (VII), has a purity of ≧99%, and was essentially free of the isomeric 4-[1-(1,3,4-triazolyl)methyl]-benzonitrile of formula (V) or its corresponding hydrochloride salt.

Furthermore, it was found that the 4-[1-(1,2,4-triazolyl)methyl]-benzonitrile hydrochloride of formula (VII) thus obtained with a purity of ≧99%, could suitably be reacted with 4-fluorobenzonitrile (VI), in presence of a suitable solvent and in presence of a suitable base at a low temperature of between −25° to +5° C., to afford Letrozole (I) of purity ≧99%, essentially free of the undesired impurities, like 4-[1-(1,3,4-triazolyl)methyl]-benzonitrile of formula (V) and Isoletrozole (IX). In all instances, it was found that Letrozole (I) is obtained in a purity of ≧99%, which is very easily amenable to a Pharmacopoeial grade, by a single crystallization, step from a suitable solvent.

SUMMARY OF THE INVENTION

In accordance with the objectives, in one aspect, the present invention relates to an improved process for preparation of 4-[1-(1,2,4-triazolyl)methyl]-benzonitrile hydrochloride of formula (VII), having a purity of ≧99%, characterized by the steps of:

i) Addition of 1H-1,2,4-triazole of formula (III), over a period of 1 to 4 hours to a mixture of 4-bromomethyl benzonitrile of formula (II), an inorganic base, selected from an alkali metal carbonate, and in presence of an organic solvent, selected from acetone or toluene at a temperature of between 20° to 50° C.;

ii) Heating the mixture of step i) at a temperature of between 50° to 110° C., for a period of 2 to 4 hours, till completion of reaction;

iii) Cooling the mixture of step ii) to ambient temperature and removal of the inorganic base by filtration;

iv) Evaporation of the solvent from the filtrate of step iii) and dissolving the residue in ethyl acetate or diluting the filtrate of step iii) with ethyl acetate;

v) Washing of the ethyl acetate solution, containing 4-[1-(1,2,4-triazolyl)methyl]-benzonitrile of formula (IV) with water two to three times and separation of the ethyl acetate layer;

vi) Cooling the ethyl acetate solution of step v) to a temperature of between 0° to 10° C.;

vii) Addition of a solution of isoprapanol-hydrochloride to the solution of step vi) at a temperature of between 0 to 5° C. over a period of between 45 to 90 minutes to adjust the pH in the range of 0 to 2;

viii) Agitation of the mixture of step vii) at a temperature of between 0° to 5° C. for period of between 1 to 2 hours;

ix) Isolation of the precipitated 4-[1-(1,2,4-triazolyl)methyl]-benzonitrile hydrochloride of formula (VII) from step viii) by filtration;

x) Optionally dissolving the solid of step ix) in ethyl acetate and treating the solution with a base to obtain 4-[1-(1,2,4-triazolyl)methyl]-benzonitrile of formula (IV) and further treating the solution with isoprapanol-hydrochloride, followed by isolation of the precipitated 4-[1-(1,2,4-triazolyl)methyl]-benzonitrile hydrochloride of formula (VII) by filtration; and xi) Drying the solid of step ix) or step x) to obtain 4-[1-(1,2,4-triazolyl)methyl]-benzonitrile hydrochloride of formula (VII), having a purity of ≧99%.

In another aspect, the present invention provides a process for preparation of Letrozole of formula (I), having a purity of ≧99%, characterized by the steps of:

a) Addition of a solution of 4-[1-(1,2,4-triazolyl)methyl]-benzonitrile hydrochloride of formula (VII), having a purity of ≧99%, in a dipolar aprotic solvent, selected from N,N-dimethylformamide or N,N-dimethylacetamide over a period of 30 to 60 minutes to a solution of potassium tertiarybutoxide in the same dipolar aprotic solvent at a temperature of between −25° to +5° C.;

b) Agitation of the mixture of step a) at a temperature of between −25° to +5° C. for a period of between 1 to 2 hours;

c) Addition of a solution of 4-fluoro benzonitrile of formula (VI) in a dipolar aprotic solvent, as used in step a over a period of 1 to 2 hours to the mixture of step b) at a temperature of between −25° to +5° C.;

d) Agitation of the mixture of step c) at a temperature of between −25° to +5° C. for a period of between 1 to 2 hours; and e) Isolation of Letrozole of formula (I) from the mixture of step d); and f) Drying the solid obtained from step e) to give Letrozole of formula (I), having a purity of ≧99%.

In yet another aspect, the present invention provides a method for preparation of Letrozole of formula (I), having a purity >99% and conforming to Pharmacopoeial specifications, by a single step crystallization from a suitable solvent of the Letrozole of purity ≧99%, obtained by the process of the present invention.

In a further aspect, the present invention provides a process for preparation of crystalline Letrozole of formula (I), having a purity of ≧99%, characterized by the X-ray (powder) diffraction pattern and DSC Thermogram, as depicted in FIG. 1 and FIG. 2, respectively.

The process for preparation of 4-[1-(1,2,4-triazolyl)methyl]-benzonitrile hydrochloride of formula (VII) and Letrozole of formula (I), both having a purity of ≧99% as per the present invention is schematically represented in Scheme-XV.

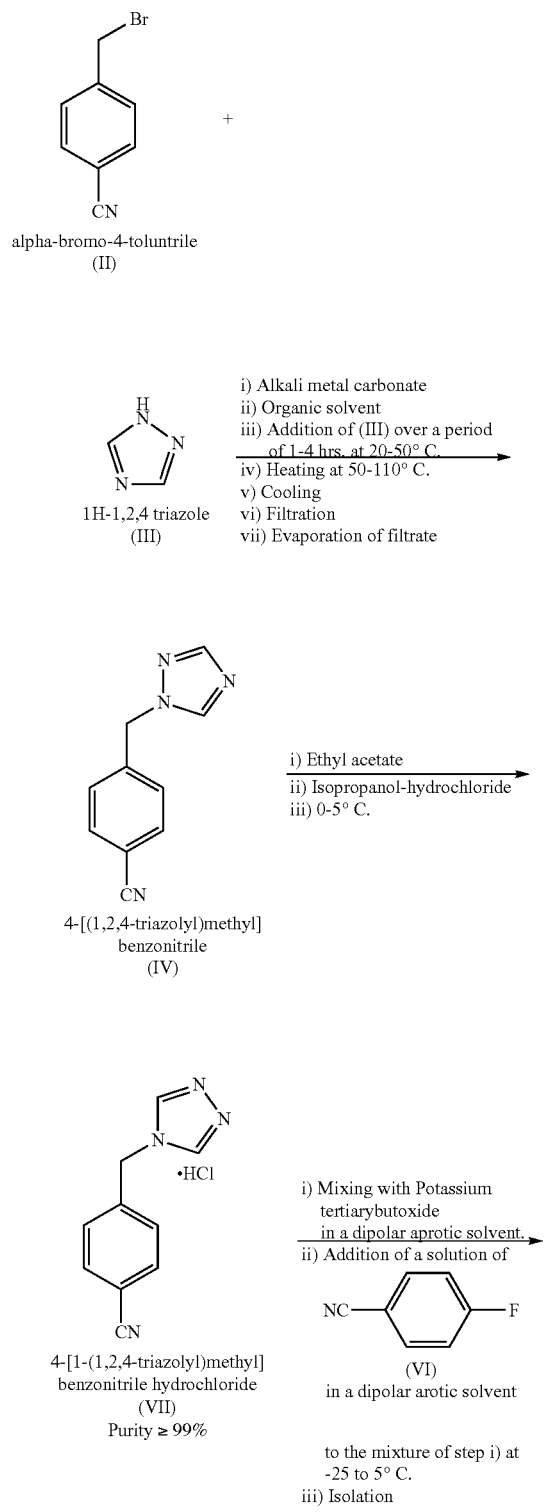

Scheme-XV: Process for Preparation of Letrozole as per the Method of the Present Invention

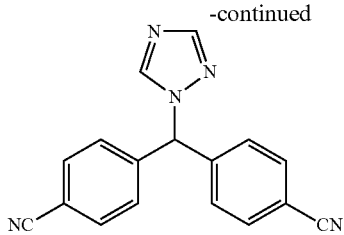

Letrozole of Purity ≥ 99% having characteristic X-ray (powder) diffraction pattern and DSC thermogram as represented in FIG. 1 & FIG. 2 respectively Single Step Crystalliztion from an Organic Solvent

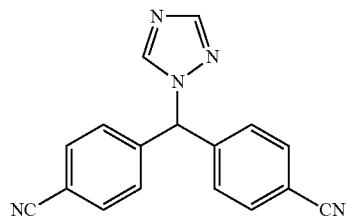

Letrozole (I) of Purity > 99% having conforming to Pharmacopoeial specifications.

DESCRIPTION OF THE DRAWINGS AND FIGURES

DETAILED DESCRIPTION OF THE INVENTION

Figure 1:
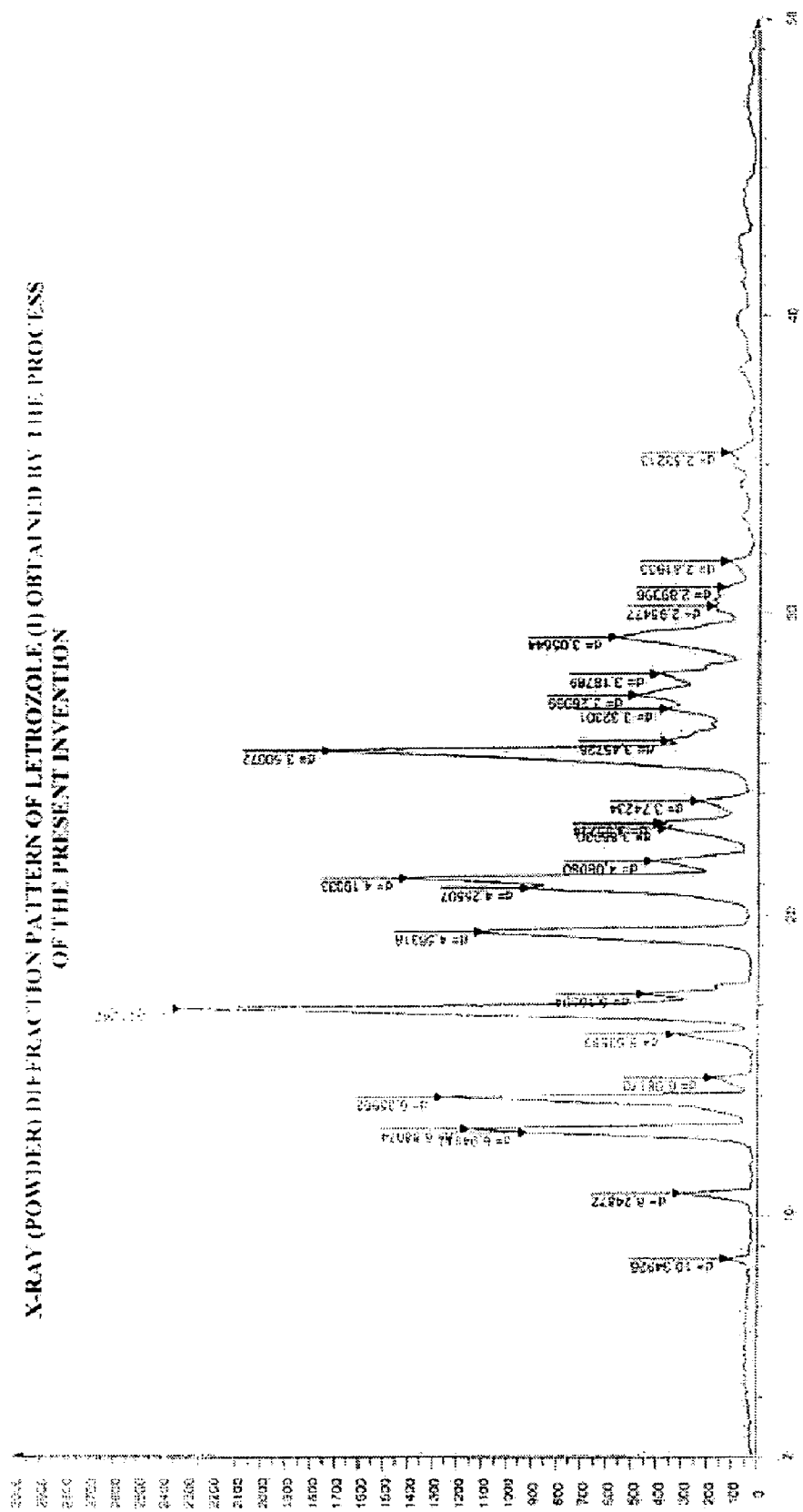
FIG. 1 is a representative X-Ray (powder) Diffraction Pattern of Letrozole of formula (I), obtained by the process of the present invention.

The present invention is detailed as hereinunder.

As evident from Scheme-XV, the process for preparation of Letrozole of formula (I), 0.10 comprises first the preparation of the intermediate compound, 4-[1-(1,2,4-triazolyl)methyl]-benzonitrile hydrochloride of formula (VII), in a purity of ≧99%, through a very simple election of a parameter, which neither contributes to an extra additional step in the process nor adds anything extra to the cost of manufacture of 4-[1-(1,2,4-triazolyl)methyl]-benzonitrile (IV), as well as 4-[1-(1,2,4-triazolyl)methyl]benzonitrile hydrochloride of formula (VII), prepared utilizing the said intermediate (IV). Secondly; the 4-[1-(1,2,4-triazolyl)methyl]benzonitrile hydrochloride of formula (VII) thus obtained with a purity of ≧99%, could suitably be reacted with 4-fluorobenzonitrile (VI), in presence of a suitable solvent and in presence of a suitable base at a low temperature of between −25° to +5° C., to afford Letrozole (I) of purity ≧99%, essentially free of the undesired impurities, like 4-[1-(1,3,4-triazolyl)methyl]-benzonitrile of formula (V) and Isoletrozole (IX). In all instances, it was found that Letrozole (I) is obtained in a purity of ≧99%, which is very easily amenable to a Pharmacopoeial grade, by a single crystallization step from a suitable solvent.

In accordance with the method of preparation of the first intermediate compound, 4-[1-(1,2,4-triazolyl)methyl]-benzonitrile (IV),

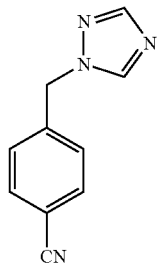

the addition of 1H-1,2,4-triazole of formula (III),

to a mixture of 4-bromomethyl benzonitrile of formula (II),

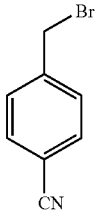

an inorganic base, and an organic solvent, is carried out slowly in lots over a period of 1 to 4 hours at a temperature of between 20° to 50° C. After complete addition of 1H-1,2,4-triazole (III), the reaction mixture is heated to a temperature of between 50° to 110° C. for a period of between 2 to 4 hours, till completion of reaction.

1H-1,2,4-triazole (III) is employed in proportions of between 1.0 to 3.0 moles per mole of 4-bromomethyl benzonitrile (II), preferably in proportions of between 1.0 to 2.5 moles per mole of 4-bromomethyl benzonitrile (II), and more preferably in proportions of between 1.0 to 1.5 moles per mole of 4-bromomethyl benzonitrile (II), The inorganic bases that are employed are selected from alkali metal carbonates, such as sodium carbonate and potassium carbonate. Typically, the alkali metal carbonate is employed in proportions of between 1.0 to 3.0 moles per mole of 4-bromomethyl benzonitrile (II), preferably in proportions of between 1.0 to 2.5 moles per mole of 4-bromomethyl benzonitrile (II), and more preferably in proportions of between 1.2 to 2.0 moles per mole of 4-bromomethyl benzonitrile (II). Of the alkali metal carbonates, potassium carbonate is the most preferred.

The organic solvents that can be utilized are selected from acetone or toluene and are typically employed in proportions of 3 to 10 times by volume of the amount of 4-bromomethyl benzonitrile (II) employed. Typically, the organic solvent is employed in proportions of 3 to 10 times by volume of the amount of 4-bromomethyl benzonitrile (II) employed.

The reaction of 4-bromomethyl benzonitrile (II) and 1H-1,2,4-triazole (III) is typically monitored by HPLC and the reaction is worked up in the following manner, after completion of the reaction, which usually is over between 2 to 4 hours.

After the completion of reaction, the reaction is cooled to ambient temperature and the insoluble inorganic base is removed by filtration. The insoluble inorganic base can be filtered through simple membrane filters or over filter aids, such as celite. The filter bed is washed with the same solvent used in the reaction and washings are combined with the principal filtrate to give the first intermediate compound, 4-[1-(1,2,4-triazolyl)methyl]-benzonitrile (IV).

The solvent can be evaporated from the combined filtrate containing the first intermediate compound, 4-[1-(1,2,4-triazolyl)methyl]-benzonitrile (IV), to dryness or near dryness and the residue is redissolved in ethyl acetate. The ethyl acetate solution is washed two to three times with water and to the combined ethyl acetate layer is cooled to a temperature of between 0° to 10° C. To the cooled solution is then added a solution of isopraponal-hydrochloride (18% w/w), slowly over a period of 45 to 90 minutes, to being the pH of the solution in the range of between 0 to 2. The mixture is agitated at the same temperature for a period of between 1 to 2 hours and the precipitated solid is collected by filtration to give the second intermediate compound, 4-[1-(1,2,4-triazolyl)methyl]-benzonitrile hydrochloride of formula (VII),

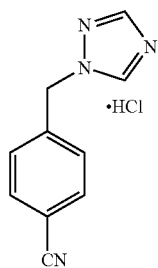

(VII)

Alternatively, ethyl acetate could be added directly to the combined filtrate containing the first intermediate compound, 4-[1-(1,2,4-triazolyl)methyl]-benzonitrile (IV), followed by washing of the solution two to three times with water and to the combined organic layer is cooled to a temperature of between 0° to 10° C. To the cooled solution is then added a solution of isopraponal-hydrochloride (18% w/w), slowly over a period of 45 to 90 minutes, to being the pH of the solution in the range of between 0 to 2. The mixture is agitated at the same temperature for a period of between 1 to 2 hours and the precipitated solid is collected to filtration to give the second intermediate compound, 4-[1-(1,2,4-triazolyl)methyl]-benzonitrile hydrochloride (VII).

The second intermediate compound, 4-[1-(1,2,4-triazolyl)methyl]-benzonitrile hydrochloride (VII) is typically obtained in purity of ≧99% and is essentially free of the isomeric 4-[1-(1,3,4-triazolyl)methyl]-benzonitrile of formula (V) or its corresponding hydrochloride salt of formula (VIII),

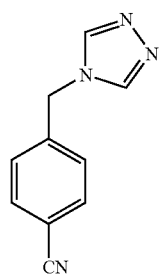

(V)

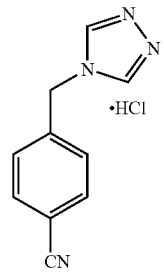

(VIII)

As mentioned hereinbefore, it was found that in the reaction of alpha-bromo-4 tolunitrile or 4-bromomethyl benzonitrile (II) with 1H-1,2,4-triazole (III) for preparation of the first intermediate, 4-[1-(1,2,4-triazolyl)methyl]-benzonitrile (IV), a very significant reduction, of more than 80%, in the formation of the undesired isomeric 4-[1-(1,3,4-triazolyl)methyl]-benzonitrile of formula (V) could be achieved simply by addition of 1H-1,2,4-triazole (III), over a period of 1 to 4 hours, at a temperature ranging from about 20° to 50° C. to a mixture of 4-bromomethyl benzonitrile (II), an alkali metal carbonate and an organic solvent, selected from acetone or toluene. The amount of the undesired isomeric 4-[1-(1,3,4-triazolyl)methyl]-benzonitrile of formula (V) formed in the reaction, through addition of 1H-1,2,4-triazole (III), over a period of 1 to 4 hours to a mixture of 4-bromomethyl benzonitrile (II) and an alkali metal carbonate in an organic solvent selected from acetone or toluene, was found to be only about 6-8%, in comparison to formation of the same in about 30-45%, when either 1H-1,2,4-triazole (III), is added in one lot or over a period less than 1 hour to a mixture of 4-bromomethyl benzonitrile (II) and an alkali metal carbonate, in the same organic solvents, both additions being carried out under identical temperatures.

Further, it was found that the level of 6-8% of the isomeric 4-[1-(1,3,4-triazolyl)methyl]-benzonitrile of formula (V), formed in the reaction, through addition of 1H-1,2,4-triazole (III) over a period of 1 to 4 hours, could be practically removed on isolation of the product i.e. 4-[1-(1,2,4-triazolyl)methyl]-benzonitrile (IV), as its hydrochloride salt i.e. 4-[1-(1,2,4-triazolyl)methyl]-benzonitrile hydrochloride of formula (VII). Typically, it was found that the isolated 4-[1-(1,2,4-triazolyl)methyl]-benzonitrile hydrochloride (VII), has a purity of ≧99%, and was essentially free of the isomeric 4-[1-(1,3,4-triazolyl)methyl]-benzonitrile of formula (V) or its corresponding hydrochloride salt of formula (VIII).

On the contrary, it was found that on conversion of the first intermediate, 4-[1-(1,2,4-triazolyl)methyl]-benzonitrile (IV), obtained by addition of 1H-1,2,4-triazole (III) in one lot or over a period less than 1 hour and containing the undesired isomeric 4-[1-(1,3,4-triazolyl)methyl]-benzonitrile of formula (V) in an amount of 30 to 45% to the corresponding hydrochloride salt, the hydrochloride salt thus obtained i.e. 4-[1-(1,2,4-triazolyl)methyl]-benzonitrile hydrochloride (VII) was found to have a purity of only 85 to 90%, and contaminated with significant amounts of the isomeric 4-[1-(1,3,4-triazolyl)methyl]-benzonitrile of formula (V) or its hydrochloride salt of formula (VIII). It was further found that the hydrochloride salt (VII) thus obtained and having a purity of 85-90% requires successive purifications or tedious chromatography to be upgraded to a purity of ≧99%, which needless to mention, is not only tedious but also results in significant yield loss.

A comparison of the method of the present invention for preparation of both 4-[1-(1,3,4-triazolyl)methyl]-benzonitrile of formula (V) and 4-[1-(1,2,4-triazolyl)methyl]-benzonitrile hydrochloride (VII), through addition of 1H-1,2,4-triazole (III) over a period of 1 to 4 hours with that for preparation of both 4-[1-(1,3,4-triazolyl)methyl]-benzonitrile of formula (V) and 4-[1-(1,2,4-triazolyl)methyl]-benzonitrile hydrochloride (VII), through addition of 1H-1,2,4-triazole (III) in one lot summarized in Table-I.

From the comparison given in Table-I, the advantages and superiority of the method of the present invention over the prior art method, especially that disclosed by Bowman et al. in U.S. Pat. No. 4,978,672, and U.S. Pat. No. 5,352,795 would be highly evident. The method of the present invention is simple, convenient and economical and most importantly, does not take recourse to any multiple and tedious crystallization and chromatographic method for preparation of both 4-[1-(1,3,4-triazolyl)methyl]-benzonitrile of formula (V) and 4-[1-(1,2,4-triazolyl)methyl]-benzonitrile hydrochloride (VII).

Further, the method of the present invention, as far as preparation of both 4-[1-(1,3,4-triazolyl)methyl]-benzonitrile of formula (V) and 4-[1-(1,2,4-triazolyl)methyl]-benzonitrile hydrochloride (VII) are concerned is distinct from the other prior art methods reported for their preparation in that:

a) It primarily achieves a significant reduction in the amount of the undesired isomeric 4-[1-(1,3,4-triazolyl)methyl]-benzonitrile (V), unlike the methods disclosed by Kompella et al. in WO 2005/047269 A1 and Haider et al. in WO 2007/054964 A2, which primarily relate to methods for separation of the undesired isomeric 4-[1-(1,3,4-triazolyl)methyl]-benzonitrile (V) from the desired 4-[1-(1,2,4-triazolyl)methyl]-benzonitrile (IV), which are tedious;

b) It primarily achieves a significant reduction in the amount of the undesired isomeric 4-[1-(1,3,4-triazolyl)methyl]-benzonitrile (V), through a very simple election of a parameter, which neither contributes to an extra additional step in the process nor adds anything extra to the cost of manufacture of 4-[1-(1,2,4-triazolyl)methyl]-benzonitrile (IV), unlike the method disclosed by Patel et al. in US 2006/0128775 A1, which involves multiple steps as well as hazardous chemical steps;

c) It primarily achieves a significant reduction the amount of the undesired isomeric 4-[1-(1,3,4-triazolyl)methyl]-benzonitrile (V), through use of inexpensive 1H-1,2,4-triazole (III), unlike the use of an alkali metal salt of 1H-1,2,4-triazole (4), as reported by Wadhwa et al. in US 2005/0209294 A1; Radhakrishnan et al. in WO 2007/039912 A1; and Macdonald et al. in US 2007/0066831 A1 and 4-amino-1,2,4-triazole (5), as reported by Patel et al. in US 2006/0128775 A1, which are costlier by nearly 4 and 3 times, respectively; and

TABLE I

Comparison Of The Method Of The Present Invention For Preparation Of Both 4-[1-(1,3,4-triazolyl)methyl]-benzonitrile (V) And 4-[1-(1,2,4-triazolyl) methyl]-benzonitrile hydrochloride (VII), Through Addition of 1H-1,2,4-triazole (III) Over A Period of 1 to 4 hours With That Wherein 1H-1,2,4-triazole (III) Is Added In One Lot

| Sr. No. | Parameter/Condition | Addition of Compound (III) In One Lot | Addition of Compound (III) In 1 To 4 Hours (Present Invention) |
|---|---|---|---|
| 01 | Molar Equivalent of 1H-1,2,4,-triazole (III) used* | 1.0 | 1.0 |
| 02 | Molar Equivalent of $K_2CO_3$ used* | 1.50 | 1.50 |
| 03 | Solvent Used and Times by Volume** | a) Acetone (5) b) Toluene (5) | a) Acetone (5) b) Toluene (5) |
| 04 | Addition temperature of 1H-1,2,4,-triazole (III) | a) 45° to 50° C. b) 25° to 30° C. | a) 45° to 50° C. b) 25° to 30° C. |
| 05 | Addition time of 1H-1,2,4,-triazole (III) | ≈ 2 Minutes | ≈ 180 Minutes |
| 06 | Reaction Temperature | a) 50° to 55° C. b) 105° to 110° C. | a) 50° to 55° C. b) 105° to 110° C. |
| 09 | Reaction Time | a) ≈ 3 Hours b) ≈ 3 Hours | a) ≈ 3 Hours b) ≈ 3 Hours |
| 10 | Amount of isomeric 4-[1-(1,3,4-triazolyl)methyl]-benzonitrile (V) formed in the reaction | a) ≈ 45% b) ≈ 42% | a) ≈ 7% b) ≈ 6% |
| 11 | Amount of isomeric 4-[1-(1,3,4-triazolyl)methyl]-benzonitrile (V) or its hydrochloride salt (VIII) present in the final product, 4-[1-(1,2,4-triazolyl) methyl]-benzonitrile hydrochloride (VII) | a) ≈ 18% b) ≈ 17% | a) <1% b) <1% |
| 12 | Purity of Isolated 4-[1-(1,2,4-triazolyl) methyl]-benzonitrile hydrochloride (VII) | a) & b) 83-85% | a) & b) ≧99% |
| 13 | Yield of 4-[1-(1,2,4-triazolyl)methyl]-benzonitrile hydrochloride (VII) | 35% | 81% |
| 13 | Requirements for Multiple Purifications or Chromatography | Required | Not Required |

*With respect to 1.0 Moles of 4-bromomethyl benzonitrile (II) used
**By Volume with respect to amount of 4-bromomethyl benzonitrile (II) used d) It primarily achieves a significant reduction the amount of the undesired isomeric 4-[1-(1,3,4-triazolyl)methyl]-benzonitrile (V), through a simple method, which does not require strict adherence to critical conditions and parameters, for the preparation of the same as reported by Pizzocaro et al. in WO 2007/090464 A1;

In accordance with another aspect of the present invention, the 4-[1-(1,2,4-triazolyl)methyl]-benzonitrile hydrochloride (VII), thus obtained is reacted with 4-fluorobenzonitrile of formula (VI), in presence of a

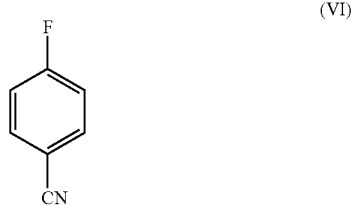

(VI)

dipolar aprotic solvent and potassium tertiarybutoxide to give Letrozole of formula (I),

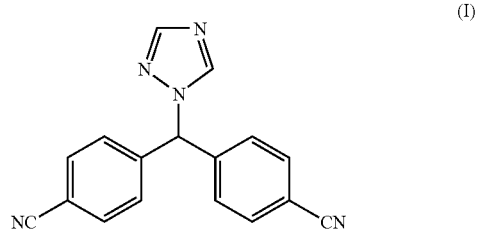

(I)

having a purity ≧99%, which is essentially free of the isomeric Isoletrozole of formula (IX).

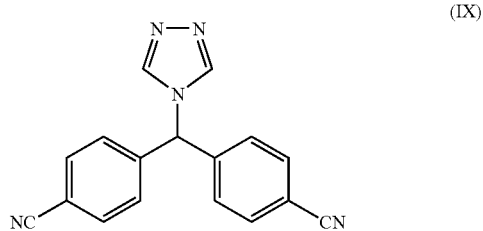

(IX)

In an embodiment, a solution of 4-[1-(1,2,4-triazolyl)methyl]-benzonitrile hydrochloride (VII), having a purity of 99% in a dipolar aprotic solvent is first added to a solution of potassium tertiarybutoxide in the same dipolar aprotic solvent over a period of 30 to 60 minutes at a temperature of between −25° to +5° C. The mixture is agitated at the same temperature for 1 to 2 hours, subsequent to which a solution of 4-fluorobenzonitrile (VI) in the same dipolar aprotic solvent is added to the mixture, over a period of between 1 to 2 hours at a temperature of between −25° to +5° C. The reaction is continued under agitation for 1 to 2 hours, when usually it gets completed and results in formation of Letrozole (I). After completion of reaction, the reaction mixture is acidified, preferably with aqueous hydrochloric acid and extracted into a water-immiscible organic solvent, which is further washed with water. Evaporation of the organic solvent and crystallization from a suitable organic solvent gives Letrozole of purity ≧99%.

The dipolar aprotic solvents that can be employed are N,N-dimethylformamide or N,N-dimethylacetamide.

Potassium tertiarybutoxide is employed in proportions of 3 to 10 moles per mole of 4-[1-(1,2,4-triazolyl)methyl]-benzonitrile hydrochloride (VII) used, preferably in proportions of 5 to 7 moles per mole of 4-[1-(1,2,4-triazolyl)methyl]-benzonitrile hydrochloride (VII).

4-fluorobenzonitrile (VI), is employed in proportions of 1 to 3 moles per mole of 4-[1-(1,2,4-triazolyl)methyl]-benzonitrile hydrochloride (VII) used, preferably in proportions of 1 to 2 moles per mole of 4-[1-(1,2,4-triazolyl)methyl]-benzonitrile hydrochloride (VII).

Suitable solvents that can be employed for crystallization of Letrozole (I), are selected from, but not limited to polar and non-polar solvents such as alcohols, ketones and esters, the preferred being ethyl acetate.

Figure 2:
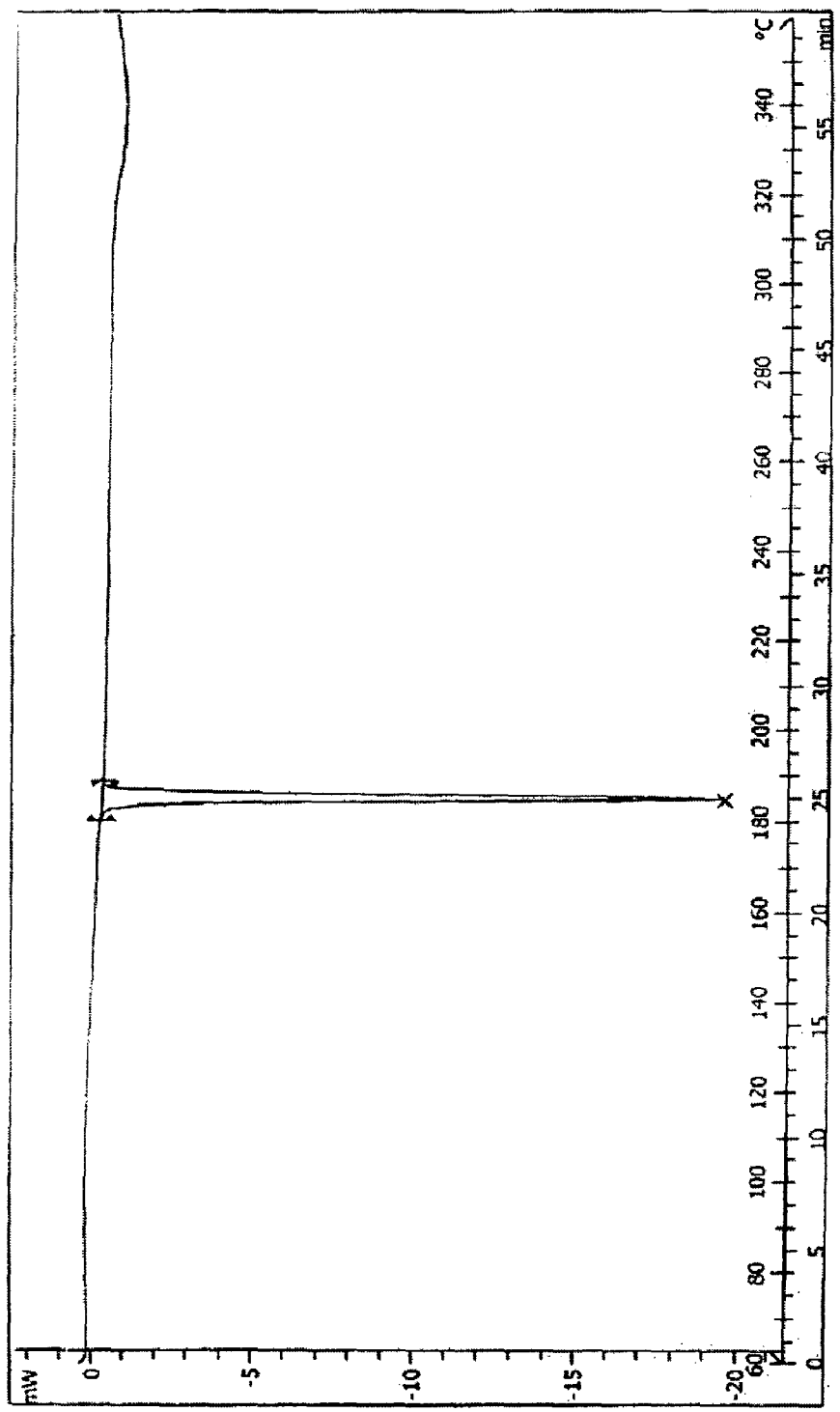
FIG. 2 is a representative DSC Thermogram of Letrozole of formula (I), obtained by the process of the present invention.

The Letrozole (I), as mentioned hereinbefore is obtained in a purity of ≧99% and is essentially free of Isoletrozole (IX) and other impurities. The Letrozole (I), thus obtained, as per the method of the present invention, is crystalline and exhibits essentially the X-ray (powder) Diffraction Pattern and DSC Thermogram, essentially as represented in FIG. 1 and FIG. 2 respectively.

The X-ray (powder) Diffraction reported herein were obtained using Cu Ka radiation, having wavelength 1.541 A° and were obtained using a D8 advanced Bruker X-ray Powder Diffractometer and comprises characteristic peaks at about 10.7, 12.8, 13.9, 16.8, 19.4, 21.1, 25.4, 27.2 and 29.1, ±0.2 degrees 2θ.

Differential Scanning Calorimetry (DSC) was carried out in a Mettler Instrument, with a ramp of 5° C./minute with a modulation time of 60 seconds and a modulation temperature of ±1° C. The starting temperature was 60° C. and the ending temperature was 360° C. Crystalline Letrozole exhibit an endothermic peak at about 183.79° C., with the onset and endset peaks at about 183.41° C. and 186.18° C. respectively.

The Letrozole (I), obtained by the process enumerated hereinbefore, and as essentially summarized in Scheme-XV could be further crystallized from a suitable solvent in a single step to give a material of Pharmacopoeial quality, generally having a purity of >99% and more in the range of between 99.5% to 99.9%. Suitable solvents that can be employed for crystallization of Letrozole (I), are selected from, but not limited to polar and non-polar solvents such as alcohols, ketones and esters, the preferred being ethyl acetate. The purified Letrozole also is crystalline and further, exhibits essentially the X-ray (powder) Diffraction Pattern and DSC Thermogram, essentially as represented in FIG. 1 and FIG. 2 respectively.

The method of the present invention, as far as preparation of Letrozole from 4-[1-(1,2,4-triazolyl)methyl]-benzonitrile hydrochloride (VII) is concerned is distinct from the other prior art methods reported for their preparation in that:

a) It does not take recourse to any chromatographic purification technique, as utilized by Palle et al. in US 2007/0100149 A1 for obtaining Letrozole of Pharmacopoeial quality. Rather, Letrozole of Pharmacopoeial quality is obtained by the process of the present invention, which does not involve a chromatographic purification technique at any stage of its preparation;

b) It does not take recourse to any oxidative step for removal of impurities, especially Isoletrozole (IX), as utilized by Hasson et al. in US 2007/0112203 A1. Rather, Letrozole of Pharmacopoeial quality is obtained by the process of the present invention, in purity of ≧99%, which is essentially free of Isoletrozle (IX), and does not involve an oxidative step at any stage of its preparation or purification;

c) It does not take recourse to any multiple crystallizations, as utilized by Friedman et al. in US 2007/0112202 A1 for removal of Isoletrozole (IX). Rather, Letrozole of purity of ≧99%, which is essentially free of Isoletrozle (IX), is obtained by the process of the present invention through a simple one step crystallization from a suitable solvent; and d) It does not take recourse to utilization of expensive and sensitive silicon amines, as reported by Srinivas et al. in WO 2007/107733 for preparation of Letrozole (I). Rather, Letrozole of purity of ≧99%, which is essentially free of Isoletrozle (IX), is obtained by the process of the present invention, which does not involve utilization of any silicon amines at any stage of its preparation.

The process for preparation of Letrozole as per the present invention is further exemplified by way of the following examples, which, in no way should be construed as limiting the scope of the invention.

Reference Example-1

Preparation of 4-(1H-1,2,4-triazol-1-ylmethyl)benzonitrile hydrochloride (VII) through addition of 1H-1,2,4-triazole in one lot To a solution of 4-bromomethyl benzonitrile (II, 500 gm; 2.5 mol) in acetone (2.5 Lt) was added potassium carbonate (528 gm; 3.82 mol) and the mixture was maintained at a temperature of 25° to 30° C. for 30 minutes under agitation. The temperature was raised to 45° to 50° C., and to the mixture was added 1H-1,2,4-triazole (III, 176 gm; 2.55 mol) in one lot in about 2 minutes time and the reaction mixture was thereafter heated under agitation at a temperature of 50° to 55° C., for 3 hours, when the reaction was found to be complete. The reaction mixture was cooled to room temperature and filtered to remove the insoluble potassium carbonate. The filter bed was washed with acetone (250 ml) and the filtrate was evaporated to dryness under reduced pressure. The residue was dissolved in ethyl acetate (3 Lt) and washed successively three times with water (4 Lt each). The ethyl acetate layer was dried over anhydrous sodium sulfate and the solution cooled to 0° to 5° C. To the cooled solution was added a solution of isopropanol hydrochloride (18% w/w) at the same temperature till the pH of the solution is adjusted between 0 and 2. The mass was agitated at 0° to 5° C. for further 6 hours and the solid was filtered, washed with cold ethyl acetate (100 ml) and dried to give the title compound (VII, 198 gm; 35.4%), with a purity of 83%.

Reference Example-2

Preparation of 4-(1H-1,2,4-triazol-1-ylmethyl)benzonitrile hydrochloride (VII) through addition of 1H-1,2,4-triazole in one lot To a solution of 4-bromomethyl benzonitrile (II, 500 gm; 2.5 mol) in toluene (2.5 Lt) was added potassium carbonate (528 gm; 3.82 mol) and the mixture was maintained at a temperature of 25° to 30° C. for 30 minutes under agitation. To the mixture was added 1H-1,2,4-triazole (III, 176 gm; 2.55 mol) in one lot in about 2 minutes time and the temperature was raised to 105° to 110° C., and the reaction mixture was thereafter heated under agitation at a temperature of 105° to 110° C., for 3 hours, when the reaction was found to be complete. The reaction mixture was cooled to room temperature and filtered to remove the insoluble potassium carbonate. The filter bed was washed with toluene (250 ml) and the filtrate was evaporated to dryness under reduced pressure. The residue was dissolved in ethyl acetate (3 Lt) and washed successively three times with water (4 Lt each). The ethyl acetate layer was dried over anhydrous sodium sulfate and the solution cooled to 0° to 5° C. To the cooled solution was added a solution of isopropanol hydrochloride (18% w/w) at the same temperature till the pH of the solution is adjusted between 0 and 2. The mass was agitated at 0° to 5° C. for further 6 hours and the solid was filtered, washed with cold ethyl acetate (100 ml) and dried to give the title compound (VII, 201 gm; 35.9%), with a purity of 85%.

Example-1

Preparation of 4-(1H-1,2,4-triazol-1-ylmethyl)benzonitrile ydrochloride (VII) Through Addition of 1H-1,2,4-triazole in 1 to 4 Hours To a solution of 4-bromomethyl benzonitrile (II, 500 gm; 2.5 mol) in acetone (2.5 Lt) was added potassium carbonate (528 gm; 3.82 mol) and the mixture was maintained at a temperature of 25° to 30° C. for 30 minutes under agitation. The temperature was raised to 45° to 50° C., and to the mixture was added 1H-1,2,4-triazole (III, 176 gm; 2.55 mol) in slowly in lots over 3 hours at the same temperature. After the complete addition, and the reaction mixture was thereafter heated under agitation at a temperature of 50° to 55° C., for 3 hours, when the reaction was found to be complete. The reaction mixture was cooled to room temperature and filtered to remove the insoluble potassium carbonate. The filter bed was washed with acetone (250 ml) and the filtrate was evaporated to dryness under reduced pressure. The residue was dissolved in ethyl acetate (3 Lt) and washed successively three times with water (4 Lt each). The ethyl acetate layer was dried over anhydrous sodium sulfate and the solution cooled to 0° to 5° C. To the cooled solution was added a solution of isopropanol hydrochloride (18% w/w) at the same temperature till the pH of the solution is adjusted to between 0 and 2. The mass was agitated at 0° to 5° C. for further 6 hours and the solid was filtered, washed with cold ethyl acetate (100 ml) and dried to give the title compound (VII, 448 gm; 80.2%), with a purity of 99.1%.

Example-2

Preparation of 4-(1H-1,2,4-triazol-1-ylmethyl)benzonitrile hydrochloride (VII) through addition of 1H-1,2,4-triazole in 1 to 4 hours To a solution of 4-bromomethyl benzonitrile (II, 500 gm; 2.5 mol) in toluene (2.5 Lt) was added potassium carbonate (528 gm; 3.82 mol) and the mixture was maintained at a temperature of 25° to 30° C. for 30 minutes under agitation. To the mixture was added 1H-1,2,4-triazole (III, 176 gm; 2.55 mol), slowly in lots over 3 hours. After the complete addition, the temperature was raised to 105° to 110° C., and the reaction mixture was thereafter heated under agitation at a temperature of 105° to 110° C., for 3 hours, when the reaction was found to be complete. The reaction mixture was cooled to room temperature and filtered to remove the insoluble potassium carbonate. The filter bed was washed with toluene (250 ml) and the filtrate was evaporated to dryness under reduced pressure. The residue was dissolved in ethyl acetate (3 Lt) and washed successively three times with water (4 Lt each). The ethyl acetate layer was dried over anhydrous sodium sulfate and the solution cooled to 0° to 5° C. To the cooled solution was added a solution of isopropanol hydrochloride (18% w/w) at the same temperature till the pH of the solution is adjusted between 0 and 2. The mass was agitated at 0° to 5° C. for further 6 hours and the solid was filtered, washed with cold ethyl acetate (100 ml) and dried to give the title compound (VII, 452 gm; 80.8%), with a purity of 99.2%.

Reference Example-3

Preparation of 4-[1-(4-cyanophenyl)-1-(1,2,4-triazol-1-yl)methyl]benzonitrile (Letrozole, I)

To a mixture of potassium tertiarybutoxide (635.92 gm; 5.66 mol) and N,N-dimethylformamide (3.75 Lt), under an atmosphere of nitrogen and cooled to a temperature of −20° to −25° C., was added 4-(1H-1,2,4-triazol-1-ylmethyl)benzonitrile hydrochloride (VII, as obtained in Reference Examples 1 or 2; 250 gm; 1.13 mol) within 5 minutes and was stirred for 60 minutes at −20° C. to −25° C. To the mixture was added 4-fluoro benzonitrile (VI, 150.9 gm; 1.24 mol) within 5 minutes and the mass agitated for an hour at −20° C. to −25° C. After completion of the reaction, pH of the mixture was adjusted to between 6.0 to 6.5 by addition of 50% aqueous hydrochloric acid, maintaining the temperature between −20° C. to 0° C. After the addition of the hydrochloric acid solution, the reaction mass was stirred for additional 30 minutes and filtered. To the filtrate was added ethyl acetate and water and the ethyl acetate layer was separated and dried over anhydrous sodium sulfate. The solvent was evaporated under vacuum to give a residual solid amounting to 179 gm (55%) of Letrozole (I), having a purity of 83%.

The solid was chromatographed over silica gel (60-120 mesh) using n-Hexane and ethyl acetate as eluent to give Letrozole (100.5 gm; 56%), having a purity of 99%.

The material (100 gm) was further dissolved in ethyl acetate (1.6 Lt) at 70° to 75° C., and the solution was filtered hot. The filtrate was evaporated under vacuum till the volume was between 200 to 220 ml. The solution was cooled to 0° to 5° C. for 4 hours, and the solid filtered, washed with cold ethyl acetate and dried to give Letrozole (I, 95 gm; 95%), having a purity of 99.6%.

Example-3

Preparation of 4-[1-(4-cyanophenyl)-1-(1,2,4-triazol-1-yl)methyl]benzonitrile (Letrozole, I)

To a mixture of potassium tertiarybutoxide (635.92 gm; 5.66 mol) and N,N-dimethylformamide (3.75 Lt), under an atmosphere of nitrogen and cooled to a temperature of −20° to −25° C., was added 4-(1H-1,2,4-triazol-1-ylmethyl)benzonitrile hydrochloride (VII, as obtained in Examples 1 or 2; 250 gm; 1.13 mol) within 5 minutes and was stirred for 60 minutes at −20° C. to −25° C. To the mixture was added 4-fluoro benzonitrile (VI, 150.9 gm; 1.24 mol) within 5 minutes and the mass agitated for an hour at −20° C. to −25° C. After completion of the reaction, pH of the mixture was adjusted to between 6.0 to 6.5 by addition of 50% aqueous hydrochloric acid, maintaining the temperature between −20° C. to 0° C. After the addition of the hydrochloric acid solution, the reaction mass was stirred for additional 30 minutes and filtered. To the filtrate was added ethyl acetate and water and the ethyl acetate layer was separated and dried over anhydrous sodium sulfate. The solvent was evaporated under vacuum to give a residual solid amounting to 244 gm (75%) of Letrozole (I), having a purity of 99%.

The material (244 gm) was further dissolved in ethyl acetate (500 ml) at 70° to 75° C., and the solution was filtered hot. The filtrate was cooled to 0° to 5° C. for 4 hours, and the solid filtered, washed with cold ethyl acetate and dried to give Letrozole (I, 221 gm; 98.6%), having a purity of 99.7%.

The invention claimed is:

1. A process for preparation of Letrozole of formula (I),

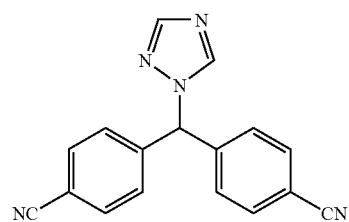

having a purity of ≧99%, comprising the steps of:
i) addition of 1H-1,2,4-triazole of formula (III),

over a period of 1 to 4 hours to a mixture of 4-bromomethyl benzonitrile of formula (II),

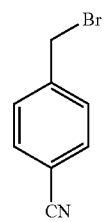

an alkali metal carbonate, and an organic solvent, at a temperature between 20° to 50° C.;
ii) heating the mixture of step i) at a temperature of between 50° to 110° C., for a period of 2 to 4 hours, till completion of reaction;
iii) cooling of the mixture of step ii) to ambient temperature and removal of the alkali metal carbonate by filtration;
iv) evaporation of the solvent from the filtrate of step iii) and dissolving the residue in ethyl acetate or diluting the filtrate of step iii) with ethyl acetate;
v) washing of the ethyl acetate solution of step iv), containing 4-[1-(1,2,4-triazolyl) methyl]-benzonitrile of formula (IV),

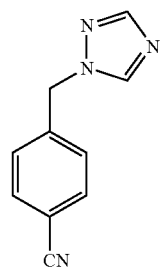

two to three times with water and separation of the ethyl acetate layer;
vi) cooling the ethyl acetate solution of step v) to a temperature of between 0° to 10° C.;

vii) addition of a solution of isopropanol-hydrochloride to the solution of step vi) at a temperature of between 0° to 5° C. over a period of between 45 to 90 minutes to adjust the pH in the range of 0 to 2;
viii) agitation of the mixture of step vii) at a temperature of between 0° to 5° C. for period of between 1 to 2 hours;
ix) isolation of 4-[1-(1,2,4-triazolyl)methyl]-benzonitrile hydrochloride of formula (VII) by filtration;

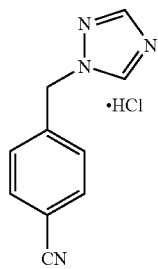

(VII)

x) optionally dissolving the solid of step ix) in ethyl acetate and treating the solution with a base to obtain 4-[1-(1,2,4-triazolyl)methyl]-benzonitrile of formula (IV),

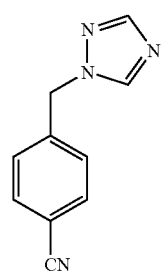

(IV)

and further treating the solution with isopropanol-hydrochloride, followed by isolation of the precipitated 4-[1-(1,2,4-triazolyl)methyl]-benzonitrile hydrochloride of formula (VII) by filtration;
xi) drying the solid of step ix) or step x) to obtain 4-[1-(1,2,4-triazolyl)methyl]-benzonitrile hydrochloride of formula (VII), having a purity of ≧99%;
xii) addition of a solution of 4-[1-(1,2,4-triazolyl)methyl]-benzonitrile hydrochloride of formula (VII), as obtained in step xi) in a dipolar aprotic solvent to a solution of potassium tertiarybutoxide in the same dipolar aprotic solvent, over a period of 30 to 60 minutes, at a temperature between −25° to 5° C.;
xiii) agitation of the mixture of step xii) at a temperature between −25° C. to 5° C. for a period of between 1 to 2 hours;
xiv) addition of a solution of 4-fluorobenzonitrile of formula (VI),

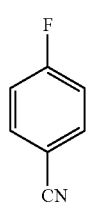

(VI)

in a dipolar aprotic solvent to the mixture of step xiii) over a period of 1 to 2 hours at a temperature of between −25° C. to 5° C.;
xv) agitation of the mixture of step xiv) at a temperature of between −25° to 5° C. for a period of between 1 to 2 hours;
xvi) isolation of Letrozole of formula (I) from the mixture of step xv); and
xvii) drying the solid obtained from step xvi) to give Letrozole of formula (I), having a purity of ≧99%.

2. The process according to claim 1, further comprising crystallization of Letrozole (I) of purity ≧99% from an organic solvent to give Letrozole (I) of purity >99%.

3. The process according to claim 1, wherein 1H-1,2,4-triazole (III) is employed in proportions of between 1.0 to 3.0 moles per mole of 4-bromomethyl benzonitrile (II).

4. The process according to claim 1, wherein 1H-1,2,4-triazole (III) is employed in proportions of between 1.0 to 1.5 moles per mole of 4-bromomethyl benzonitrile (II).

5. The process according to claim 1, wherein the alkali metal carbonate is selected from potassium carbonate or sodium carbonate.

6. The process according to claim 1, wherein the alkali metal carbonate is employed in proportions of between 1.0 to 3.0 moles per mole of 4-bromomethyl benzonitrile (II).

7. The process according to claim 1, wherein the alkali metal carbonate is employed in proportions of between 1.2 to 2.0 moles per mole of 4-bromomethyl benzonitrile (II).

8. The process according to claim 1, wherein the organic solvent is selected from acetone or toluene.

9. The process according to claim 1, wherein 4-fluorobenzonitrile (VI) is employed in proportions of 1 to 3 moles per mole of 4-[1-(1,2,4-triazolyl)methyl]-benzonitrile hydrochloride of formula (VII).

10. The process according to claim 1, wherein 4-fluorobenzonitrile (VI) is employed in proportions of 1 to 2 moles per mole of 4-[1-(1,2,4-triazolyl)methyl]-benzonitrile hydrochloride of formula (VII).

11. The process according to claim 1, wherein potassium tertiarybutoxide is employed in proportions of 3 to 10 moles per mole of 4-[1-(1,2,4-triazolyl)methyl]-benzonitrile hydrochloride of formula (VII).

12. The process according to claim 1, wherein potassium tertiarybutoxide is employed in proportions of 5 to 7 moles per mole of 4-[1-(1,2,4-triazolyl)methyl]-benzonitrile hydrochloride of formula (VII).

13. The process according to claim 1, wherein the dipolar aprotic solvent is selected from N,N-dimethylformamide or N,N-diemthylacetamide.

14. The process according to claim 2, wherein the organic solvent for crystallization of Letrozole (I) is selected from polar and non-polar solvents.

15. The process according to claim 2, wherein the organic solvent is selected from alcohols, ketones and esters.

16. The process according to claim 15, wherein the organic solvent is ethyl acetate.

* * * * *